(12) United States Patent
Van Praet et al.

(10) Patent No.: US 10,222,375 B2
(45) Date of Patent: Mar. 5, 2019

(54) PROCESS AND MACHINE FOR AUTOMATED AGGLUTINATION ASSAYS WITH IMAGE AUTOMATED EVALUATION

(71) Applicant: Gold Standard Diagnostics, Davis, CA (US)

(72) Inventors: Peter Van Praet, Hassrode (BE); Jennifer Roth, Sacramento, CA (US); John Griffiths, Davis, CA (US)

(73) Assignee: Gold Standard Diagnostics, Davis, CA (US)

( * ) Notice: Subject to any disclaimer, the term of this patent is extended or adjusted under 35 U.S.C. 154(b) by 179 days.

(21) Appl. No.: 15/465,342

(22) Filed: Mar. 21, 2017

(65) Prior Publication Data

US 2017/0192002 A1    Jul. 6, 2017

Related U.S. Application Data

(63) Continuation-in-part of application No. 14/334,316, filed on Jul. 17, 2014, now abandoned.

(60) Provisional application No. 61/847,469, filed on Jul. 17, 2013, provisional application No. 62/421,060, filed on Nov. 11, 2016.

(51) Int. Cl.
| | | |
|---|---|---|
| *G01N 21/82* | (2006.01) | |
| *G01N 33/571* | (2006.01) | |
| *G06T 7/60* | (2017.01) | |
| *G01N 21/25* | (2006.01) | |
| *G01N 15/00* | (2006.01) | |
| *G01N 35/00* | (2006.01) | |

(Continued)

(52) U.S. Cl.
CPC ......... *G01N 33/571* (2013.01); *G01N 21/253* (2013.01); *G01N 21/82* (2013.01); *G06T 7/60* (2013.01); *G01N 2015/0092* (2013.01); *G01N 2021/825* (2013.01); *G01N 2035/00524* (2013.01); *G01N 2035/0418* (2013.01); *G01N 2035/1039* (2013.01)

(58) Field of Classification Search
None
See application file for complete search history.

(56) References Cited

U.S. PATENT DOCUMENTS

| | | |
|---|---|---|
| 3,635,446 A | 1/1972 | Kurosawa |
| 5,104,621 A | 4/1992 | Pfost |
| | (Continued) | |

*Primary Examiner* — Erik B Crawford
(74) *Attorney, Agent, or Firm* — Heisler & Associate

(57) ABSTRACT

The machine is configured to perform an automated rapid plasma reagent (RPR) agglutination test or other agglutination test. The machine includes a sample rack with multiple sample locations thereon and a reagent rack for storing of reagent. A shaker assembly supports at least one microtiter plate or other well supporting structure thereon with a plurality of wells in the plate. An automated pipette accesses samples and reagent and deposits them within wells of the microtiter plate. The shaker assembly shakes multiple samples within the wells of the microtiter plate. Finally, a camera photographs the wells of the plate, preferably from above with a light source below and the plate at least partially transparent. The image is then analyzed in an automated fashion to determine whether a ring of contrast material has remained smooth indicative of a non-reactive sample or has agglutinated/clumped together indicative of a reactive sample.

20 Claims, 21 Drawing Sheets
(14 of 21 Drawing Sheet(s) Filed in Color)

Radial lines for finding ring

(51) Int. Cl.
   *G01N 35/04*    (2006.01)
   *G01N 35/10*    (2006.01)

(56) References Cited

U.S. PATENT DOCUMENTS

| | | |
|---|---|---|
| 5,275,951 A | 1/1994 | Chow |
| 5,922,284 A | 7/1999 | Kinoshita |
| 2008/0006653 A1 | 1/2008 | Dai |
| 2009/0088336 A1 | 4/2009 | Burd |
| 2011/0015091 A1 | 1/2011 | Glezer |
| 2012/0258552 A1 | 10/2012 | Takahashi |
| 2012/0282684 A1 | 11/2012 | Fritchie |
| 2014/0273027 A1* | 9/2014 | Kiefer ................. G01N 33/571 435/7.92 |

* cited by examiner

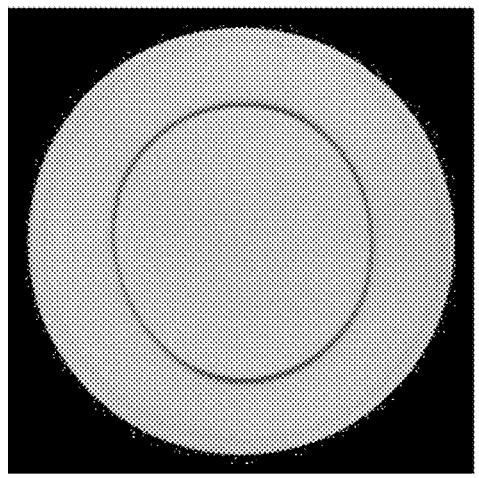
*Fig.6* Non-Reactive Sample (NR)
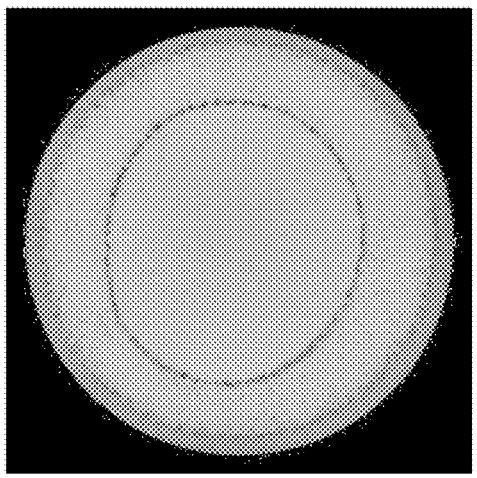
*Fig.7* Medium Reactive Sample
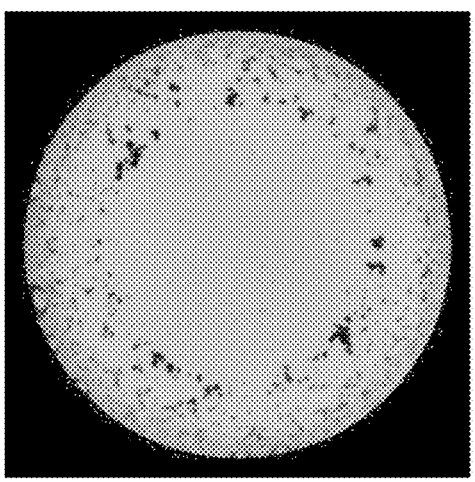
*Fig.8* Strong Reactive Sample (R)
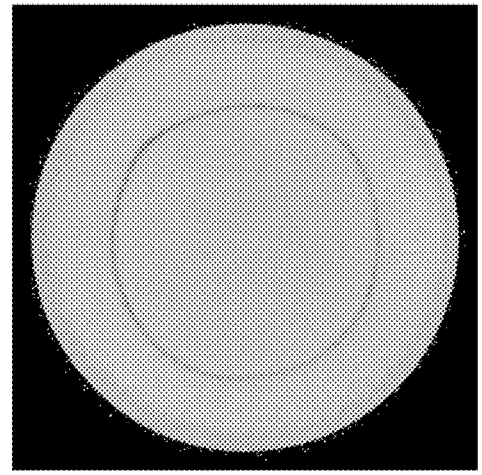
*Fig.9* Weak Reactive Sample 1
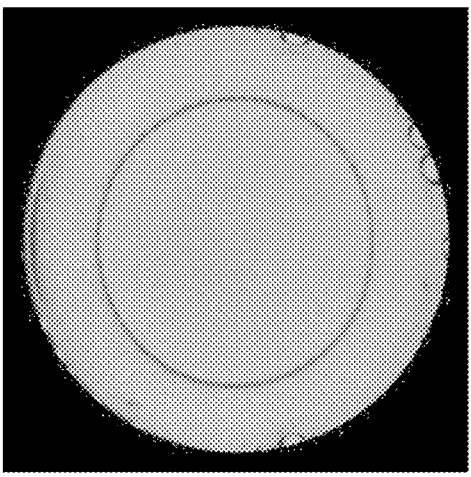
*Fig.10* Weak Reactive Sample 2
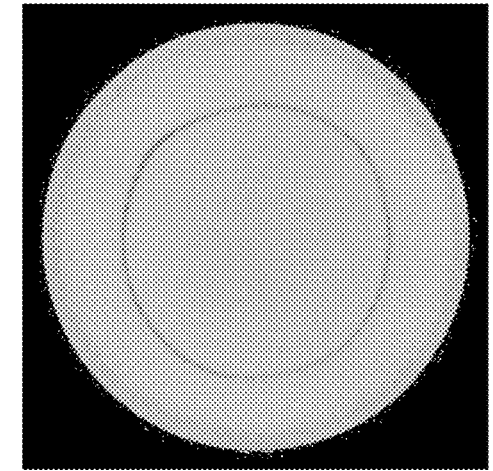
*Fig.11* Weak Reactive Sample 3

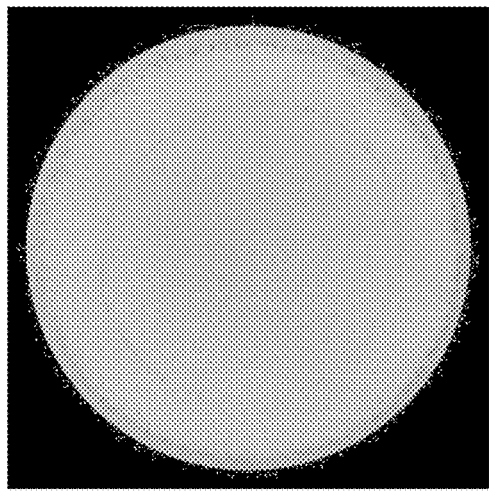
*Fig.12* Borderline Sample 1
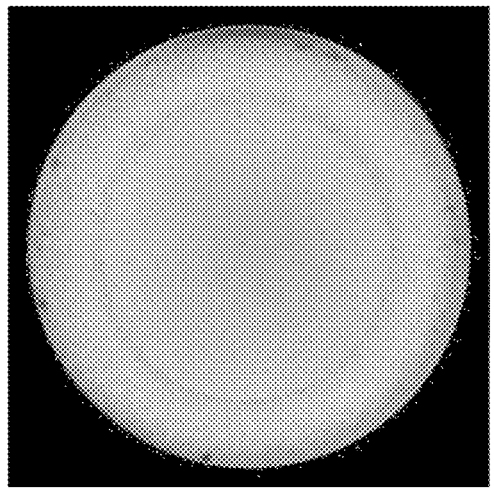
*Fig.13* Borderline Sample 2
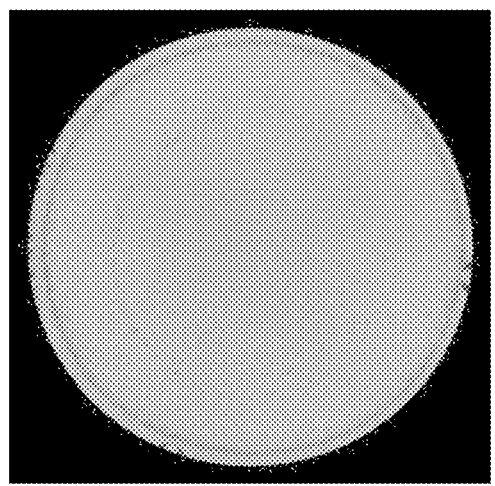
*Fig.14* Borderline Sample 3
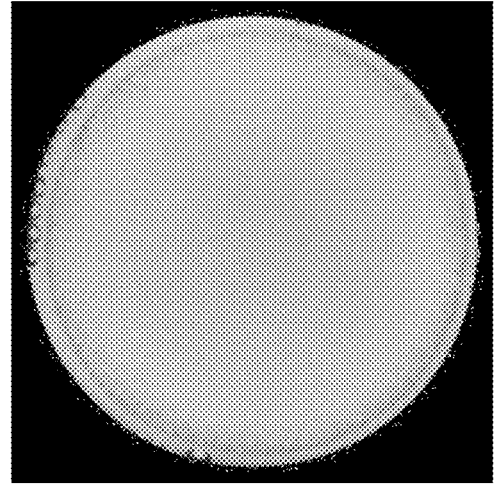
*Fig.15* No Reaction 1
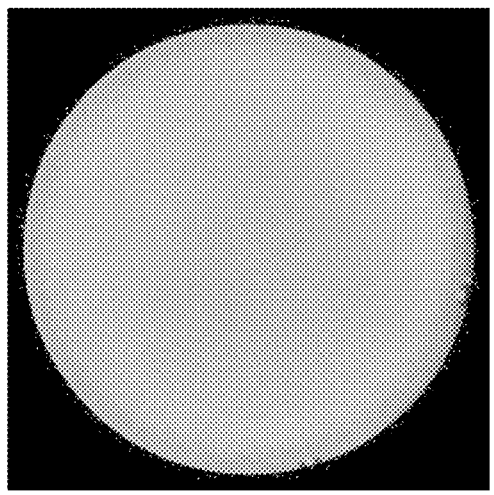
*Fig.16* No Reaction 2
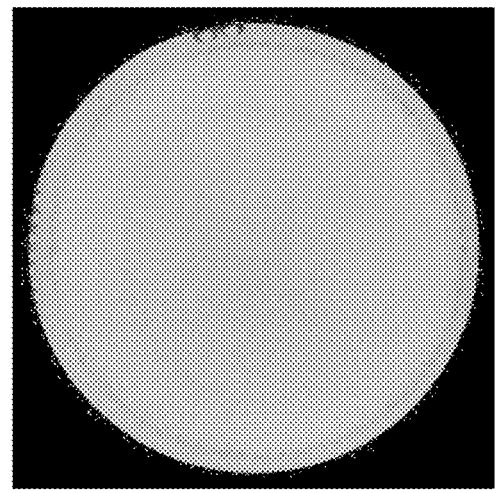
*Fig.17* No Reaction 3

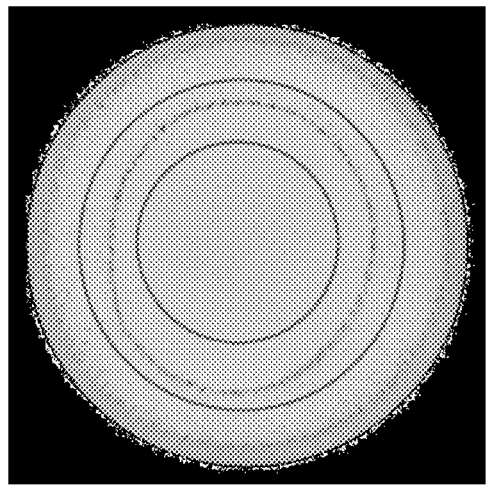
*Fig.18*
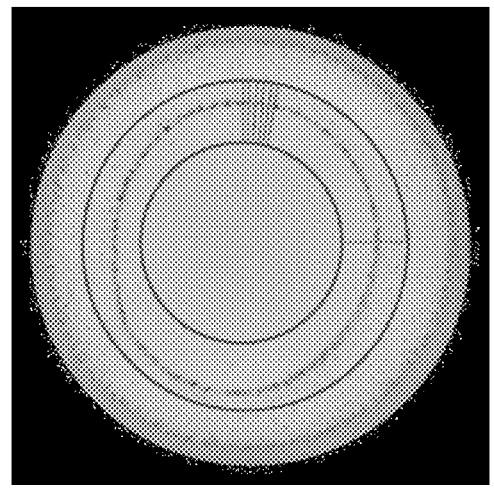
*Fig.19* Radial lines for finding ring
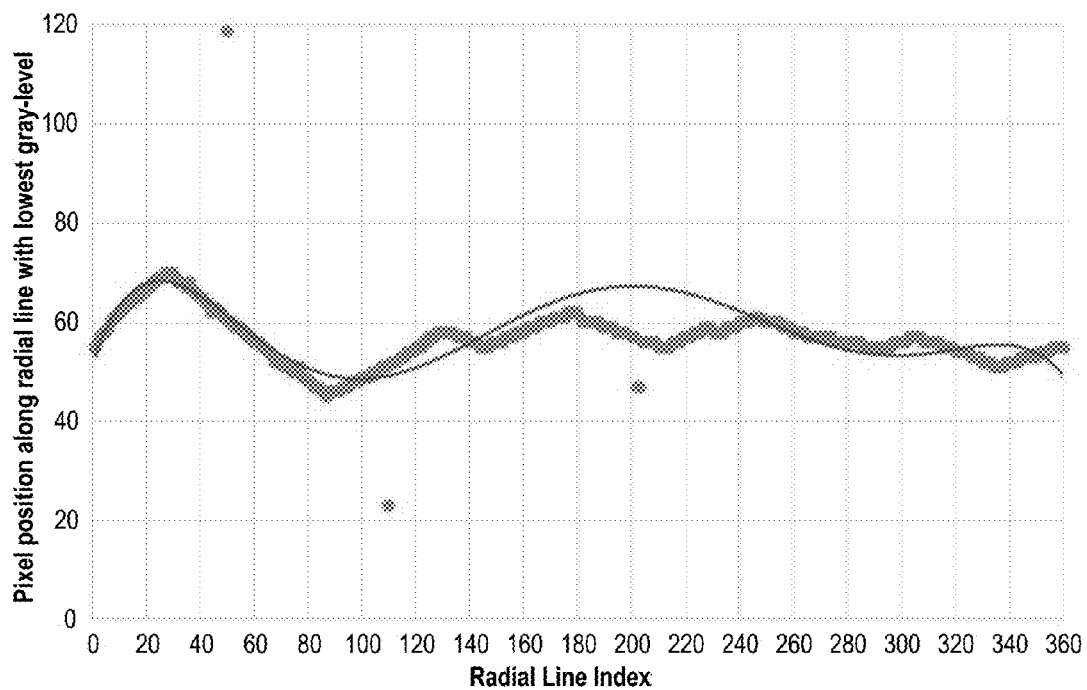
*Fig.20*

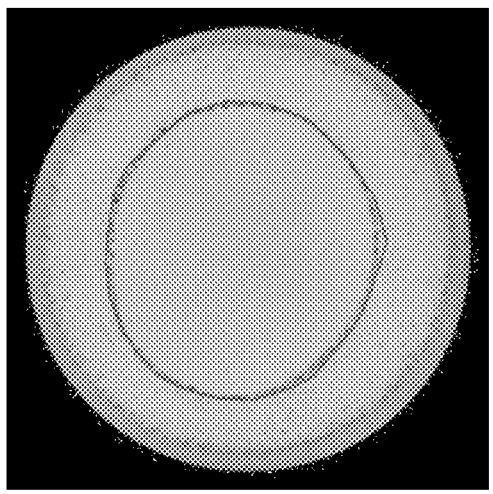
*Fig.21* Found agglutination ring
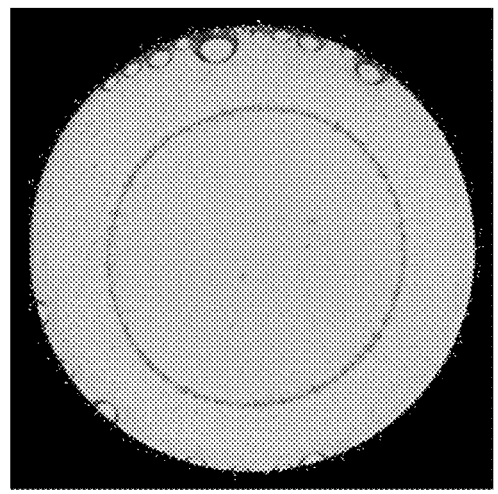
*Fig.22* Radial lines along polynomial curve defining area to examine for agglutination
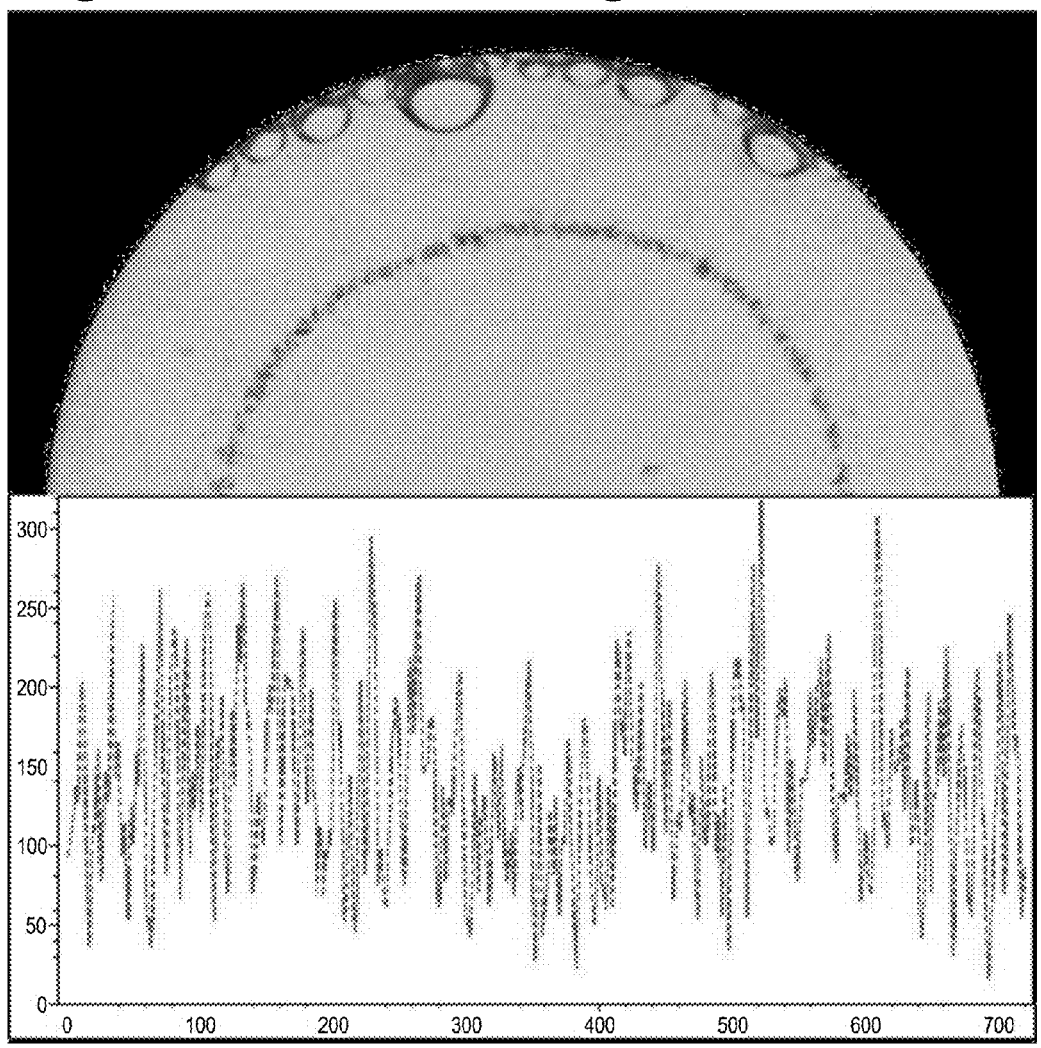
*Fig.23* Histogram of CVs of radial line gray-levels Radial lines along outer ring area to examine for agglutination Histogram of differences of BorderRingCV values and Progressive Average of those values

PROCESS AND MACHINE FOR AUTOMATED AGGLUTINATION ASSAYS WITH IMAGE AUTOMATED EVALUATION

CROSS-REFERENCE TO RELATED APPLICATIONS

This application is a continuation-in-part of U.S. patent application Ser. No. 14/334,316, filed on Jul. 17, 2014 which claims benefit under Title 35, United States Code § 119(e) of U.S. Provisional Application No. 61/847,469 filed on Jul. 17, 2013. This application also claims benefit under Title 35, United States Code § 119(e) of U.S. Provisional Application No. 62/421,060 filed on Nov. 11, 2016.

FIELD OF THE INVENTION

The following invention relates to machines and automated processes for performing automated agglutination assays, such as those used in a rapid plasma reagin (RPR) test. More particularly, this invention relates to machines and processes for automated conducting of assays such as a BD Macro-Vue RPR test, such as that utilized to detect syphilis. This system also relates to automated sample image evaluation processes to automatically determine whether or not a sample is reactive.

BACKGROUND OF THE INVENTION

Etiological agents responsible for various infections and other diseases, such as syphilis can be detected in a test referred to as a rapid plasma reagin (RPR) test. One specific such assay is known as a BD Macro-Vue RPR test provided by Becton Dickinson and Company of Franklin Lakes, N.J. The RPR test is a non-treponemal flocculation test that is used to detect and quantify reagin, an antibody present in serum or plasma as a screen test for syphilis. The etiological agent responsible for syphilis produces at least two kinds of antibodies in human infections. The treponemal antibodies can be detected by florescent treponemal antibody-absorption (FTA-ABS) test whereas the reagin antibody is detected by the RPR antigen test. In the presence of the reagin antibody and the reactive sample, the RPR antigen preparation will produce flocculation consisting of black clumps against the white background of a test card. By contrast, non-reactive samples will yield an even light gray homogenous suspension.

The RPR test known in the prior art is performed upon EDTA plasma and unheated or heated serum. The specimen should be free of bacterial contamination and haemolysis. A reagent is also utilized in the test. One such reagent is an RPR carbon antigen formed of 0.003 percent cardiolipin, 0.020-0.022 percent lecithin, 0.09 percent cholesterol, 0.0125 M EDTA, 0.1 $MNa_2HPO_4$, 0.01 $MKH_2PO_4$, 0.1 percent thimerosal, 0.0188 percent charcoal and ten percent choline chloride.

In performing the test the specimen and the reagent are combined together on a test card, such as by applying a drop of each onto the test card. The sample and antigen reagent are not mixed. Rather, they are put onto an automatic rotator, preferably under a humidity cover, with the rotator rotating the combination of the sample and reagent at 100 rpm for eight minutes. Following rotation, a brief hand rotation and tilting of card (three to four times) should be made to aid in differentiating non-reactive from minimally reactive results. Results are then read by studying the combination of the sample and the reagent. A non-reactive sample will have no clumping of the carbon particles in the reagent or very slight roughness, with a smooth gray overall appearance. If the sample is reactive, presence of large aggregates of carbon particles will be visually detected and usually against a clear background. A reactive specimen is considered to have undergone agglutination. In a more detailed variation of the test for more quantitative results, the sample is diluted two to one, four to one, eight to one, sixteen to one, etc. and the reagent is added and after rotation the sample is read for agglutination. In such a test those specimens which are non-reactive can be distinguished from those which are reactive and also minimally reactive specimens can be identified where there is a presence of small or fine aggregates of carbon particles.

Such a test involves combining a sample of a prepared blood product with an appropriate reagent that includes carbon (e.g. charcoal) particles therein. The reagent may or may not react with the specimen by undergoing flocculation. If the carbon particles become trapped in the flocculation and appear agglutinated or as black clumps against a light background, the specimen is considered to be reactive with the reagent. If the reagent maintains a uniform light gray color with even particle distribution and no clumping, it is indicative of a non-reactive specimen.

RPR tests, are currently known to be performed manually and to involve a variety of steps where the potential for human error or variation in manual performance of the test can result in less reliable results. Also, the test is significantly time intensive even when properly performed, requiring significant amounts of time expenditure by well trained practitioners. Accordingly, a need exists for an RPR test which produces a result which can be more easily read reliably by personnel with less training. Furthermore, a need exists to automate the RPR test to more rapidly and reliably conduct tests with fewer skilled operator hours being required. Furthermore, it is desirable to have test results archived in a variety of different ways for later analysis and for verification of test results. By automating the RPR test, an opportunity is presented for high quality archiving of large numbers of assays for efficient and reliable management of test results from RPR tests or agglutination assays.

SUMMARY OF THE INVENTION

With this invention a process is provided for automated agglutination assay performance for use in tests such as an RPR test, as well as a robotic analyzer for automating the performance of the processes of this invention. The process generally involves a series of steps which can be performed in sequence by the machine of this invention or a related machine for multiple samples. The sequence for one sample can overlap with the sequence for other samples in the same machine to maximize efficacy.

In one embodiment the steps are generally defined as loading samples/specimens into a sample rack of a machine, loading reagent into a reagent rack of the machine, loading a microtiter plate (or other structure with one or more wells or other test locations therein) onto a shaker assembly of the machine, using an automated microsyringe (or other aspirator and dispenser) to gather a sample from the sample rack and reagent from the reagent rack and deposit the combined sample and reagent in a well of the microtiter plate, shaking the microtiter plate for a predetermined amount of time, detect agglutination such as by photographing the well of the microtiter plate, reading the photograph for a result (reactive or non-reactive) and archiving the photograph and/or result within a database.

One machine capable of housing a plurality of samples, the reagent, and also to carry the shaker assembly and a carriage for automated motion of the microsyringe and camera is disclosed herein in a preferred embodiment. The machine has an overall housing with a lower region, a mid-region and an upper region. The lower region includes at least one sample rack with multiple locations therein. Most preferably, this sample rack is a "smart rack" which can carry test tubes or other containers of samples which can themselves have a bar code thereon and a scanner is built into the machine so that the samples are intelligently known by the machine to be positioned wherever they are placed within the rack. The reagent rack is also preferably in this lower region of the enclosure of the machine.

A midlevel of the machine preferably supports a shaker assembly thereon. This shaker assembly preferably only has half of a depth of the overall enclosure and can move forward and rearward. In this way, all of the sample racks and reagent rack locations can be accessed by moving the shaker assembly out of the way (either forward or backward). The shaker assembly is configured to support at least one microtiter plate thereon with each microtiter plate including a plurality of wells thereon. The shaker assembly is also configured with a shaker motor which can shake the microtiter plates upon the shaker assembly.

An upper portion of the enclosure has a carriage therein which preferably supports both an automated syringe, such as a microsyringe, and a camera. The carriage is configured to allow the microsyringe and camera to move both laterally and forwardly and rearwardly to access each of the samples of the sample rack, each of the wells of the microtiter plates on the shaker assembly and each of the reagent containers within the reagent rack. Appropriate robotics cooperate with the carriage and the shaker assembly to cause the microsyringe to move where required to gather a sample and reagent, and deposit them on an appropriate one of the wells within one of the microtiter plates. The robotic equipment then causes one or more combined specimen and reagent combinations to be shaken by the shaker assembly for a predetermined amount of time. A camera is then carried by the carriage to appropriate locations for photographing the wells of the microtiter plate. In a preferred embodiment the shaker assembly is configured with a diffuser beneath an at least partially transparent microtiter plate and with at least one LED light source below the diffuser, so that the wells of the microtiter plate are backlit during the photographing process.

After the process is complete, the sample ends up with the charcoal particles or other contrasting elements contained within the reagent, which have a common density, forming a ring (or at least a portion of a ring) within the microtiter plate or other sample containment well. If the sample is reactive and agglutination has taken place, this ring will have significant clumping, so that the charcoal particles or other contrasting agent will be clumped together into concentrated locations which will typically generally be arranged in a ring within the well or other sample containment area. If the sample is non-reactive, charcoal particles or other contrasting agent will form a smooth and substantially uniform ring within the sample containment space.

In simple embodiments of this invention, a user could merely view the sample and make a determination as to whether the sample is reactive or non-reactive based on whether the charcoal or other contrasting agent has clumped together indicative of agglutination and a reactive sample, or if the ring is smooth and the charcoal or other contrasting agent has not clumped together, so that the sample is non-reactive (potentially also a slightly clumped contrasting agent might indicate a minimally or weakly reactive sample). Similarly, a photograph can be taken of the sample and then the photograph of this sample could be viewed by an individual, either located at a common location with the sample or at some remote location. However, most preferably such reading of the sample as being reactive or non-reactive is at least assisted by automated evaluation of the appearance of the sample after completion of the above-process.

Automated evaluation/interpretation can occur as follows in a preferred embodiment. A digital image of the sample is taken after the sample has been processed according to the process identified above. This photograph is preferably a high contrast photograph which has the camera located on one side of a sample containment area and with a backlight on a side of the sample containment area opposite the camera. Other arrangements for lighting and positioning of the camera can be selected so that the sample can be clearly recorded as to visual appearance within a digital image created by the camera. While the image is preferably a digital image taken directly by the camera, the camera could conceivably take some form of non-digital image and then some form of digitizer could be utilized to convert such an initial non-digital image into a digital image for further processing.

A series of steps are performed in evaluating the image of the sample to determine whether the sample is reactive or non-reactive. Before these steps are performed, some pre-processing occurs including centering the well or other sample containment area at a middle of the image, compensating for non-uniform background illumination, and masking zones of non-interest, such as by blacking out corners of a typically square image so that the central circular portions of the well are all that remain as not blacked out. After such pre-processing, a series of steps are performed to manipulate and evaluate the image of the sample and to quantify different characteristics of the image of the sample. Such sample characteristics are then compared to a known prior data set of samples where status as reactive or non-reactive is known, so that the system can finally output a reactive or non-reactive result for the sample associated with the image, to a high probability of accuracy. Such interpretation of the sample image occurs in an automated fashion and can be utilized for automated outputting of results or can be utilized for support of a visual evaluation, such as to double check work of a human evaluator, or to pre-analyze samples before further review by a human evaluator.

OBJECTS OF THE INVENTION

Accordingly, a primary object of the present invention is to provide a process for automating an RPR agglutination test.

Another object of the present invention is to perform an RPR agglutination test in a reliable fashion.

Another object of the present invention is to perform an RPR agglutination test with more rapid throughput of multiple samples.

Another object of the present invention is to provide an RPR agglutination test which records results of the test in a manner allowing review of both test results and underlying photographic data upon which test result conclusions are based.

Another object of the present invention is to provide a machine which automates an RPR agglutination test.

Another object of the present invention is to provide a machine which accurately performs multiple RPR agglutination tests on multiple separate samples accurately and efficiently.

Another object of the present invention is to provide a machine and process for performing an RPR agglutination test which minimizes the potential for human error in performing the test.

Another object of the present invention is to provide a process for evaluating an image of a sample produced by performance of an agglutination assay which determines whether the sample is reactive or not in an automated fashion.

Another object of the present invention is to assist a human evaluator by providing an automated evaluation as to the reactivity of a sample.

Another object of the present invention is to provide an automated system which can analyze an image of a sample which has undergone an agglutination assay to interpret the reactivity of the sample.

Another object of the present invention is to provide a system for evaluating whether a ring of contrasting particles within a sample is exhibiting a reactive agglutinated ring of such particles or if the particles are not agglutinated and indicative of a non-reactive sample with the contrasting elements appearing as a more smooth ring.

Other further objects of the present invention will become apparent from a careful reading of the included drawing figures, the claims and detailed description of the invention.

BRIEF DESCRIPTION OF THE DRAWINGS

The patent or application file contains at least one drawing executed in color. Copies of this patent or patent application publication with color drawings will be provided by the office upon request and payment of the necessary fee.

FIGS. 6-17 are photographs of a well of a microtiter plate, such as that used with the machine of this invention, taken after a sample and a reagent have been placed in the well and after shaking to produce a ring of contrast agent. These images could be manually read or fed to a machine for automated reading.

FIG. 18 shows the sample of FIG. 7 after a step of adding concentric circular lines, shown in red, bounding regions of contrast agent concentration.

FIG. 19 shows the sample of FIG. 18 after a further step of drawing radial lines, shown in blue, perpendicular to the red circular lines of FIG. 18 and also shown in FIG. 19.

FIG. 20 is a histogram of radial position of concentrated agent, one for each radial line of FIG. 19, according to a further step, and with a curve fitted to the histogram, shown in red.

FIG. 21 shows the fitted curve, shown in red, plotted in circular coordinates overlying the photograph of the sample of FIG. 7 according to a further strep, to verify that the curve follows the ring of concentrated contrast agent presence.

FIG. 22 shows the sample of FIG. 7 according to a further step with radial lines, shown in yellow, perpendicular to the fitted curve (shown in red) and extending inward and outward from the fitted curve a similar distance for each radial line.

FIG. 23 is a histogram overlaid upon the photograph of the sample shown in FIG. 7, with the histogram plotting in red the coefficient of variation (CV) for the darkest pixels along each radial line upon the image of FIG. 22.

DESCRIPTION OF THE PREFERRED EMBODIMENT

Figure 5:
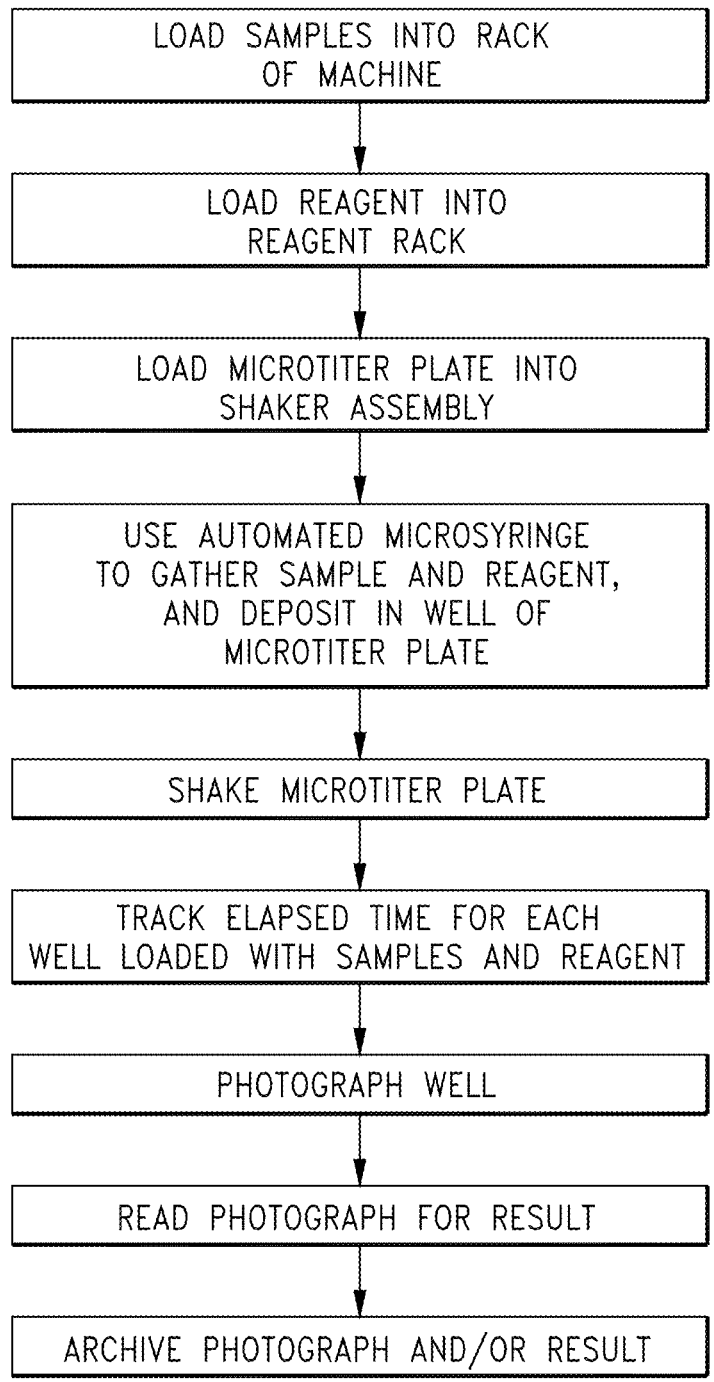
FIG. 5 is a flow chart depicting the steps in the automated agglutination test of this invention.

Referring to the drawings, wherein like reference numerals represent like parts throughout the various drawing figures, reference numeral 10 (FIG. 1) is directed to a machine for implementing an automated agglutination test process (FIG. 5) of this invention. The machine 10 can be loaded with samples, such as within the sample rack 12 and has multiple wells 32 upon a microtiter plate 30 where samples can be combined with a reagent and shaken a specified time according to the particular agglutination test protocol, such as for an RPR agglutination test. A camera 40 takes photographs of wells 32 within the microtiter 30 to record results of the test.

Figure 1:
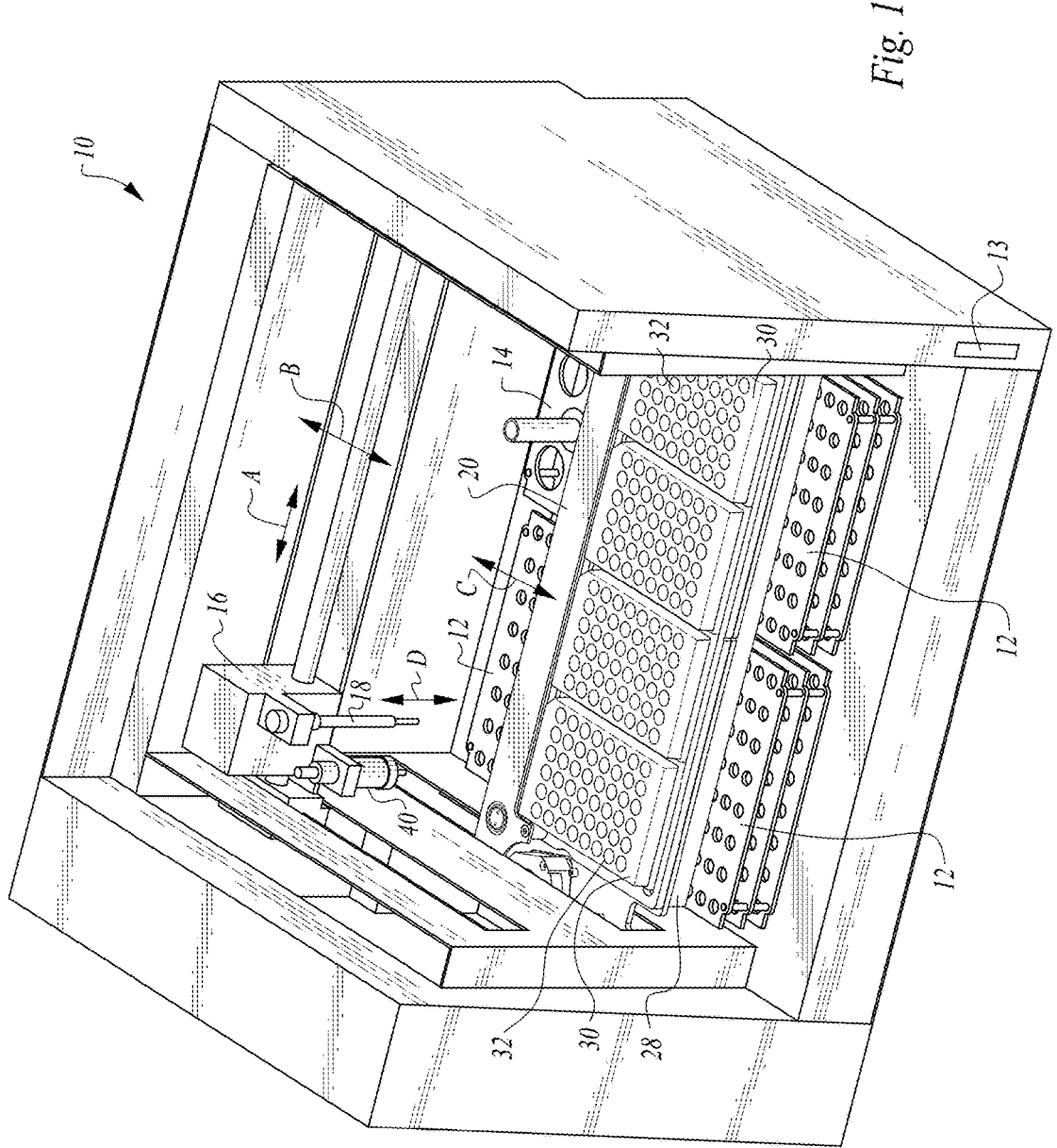
FIG. 1 is a perspective view of a machine according to this invention which can perform an RPR or other agglutination test on multiple samples in an automated fashion.
Figure 2:
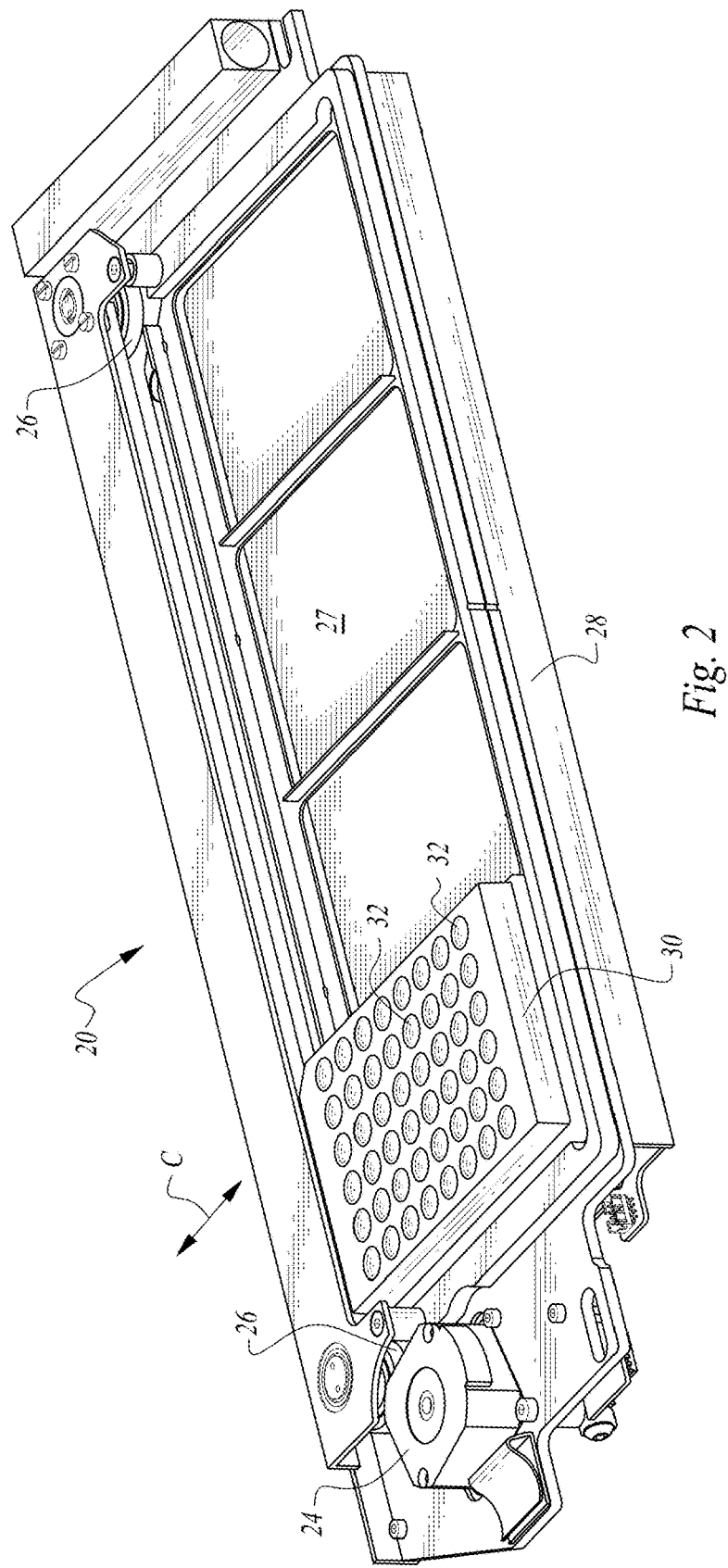
FIG. 2 is a perspective view of a shaker assembly within a midlevel of the machine of FIG. 1 and with a single microtiter plate loaded thereon.
Figure 3:
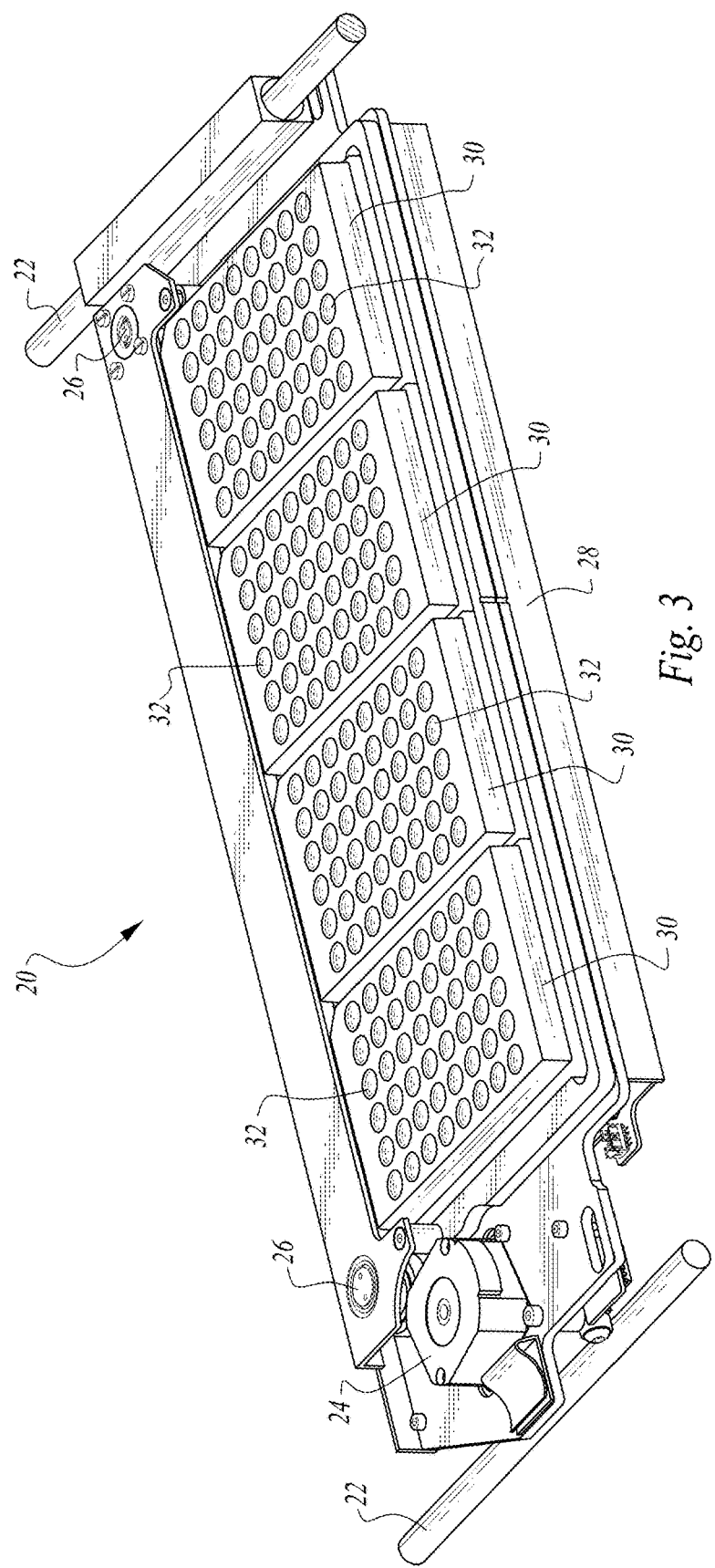
FIG. 3 is a perspective view of that which is shown in FIG. 2 but with four microtiter plates located thereon and showing rails upon which the shaker assembly is carried.
Figure 4:
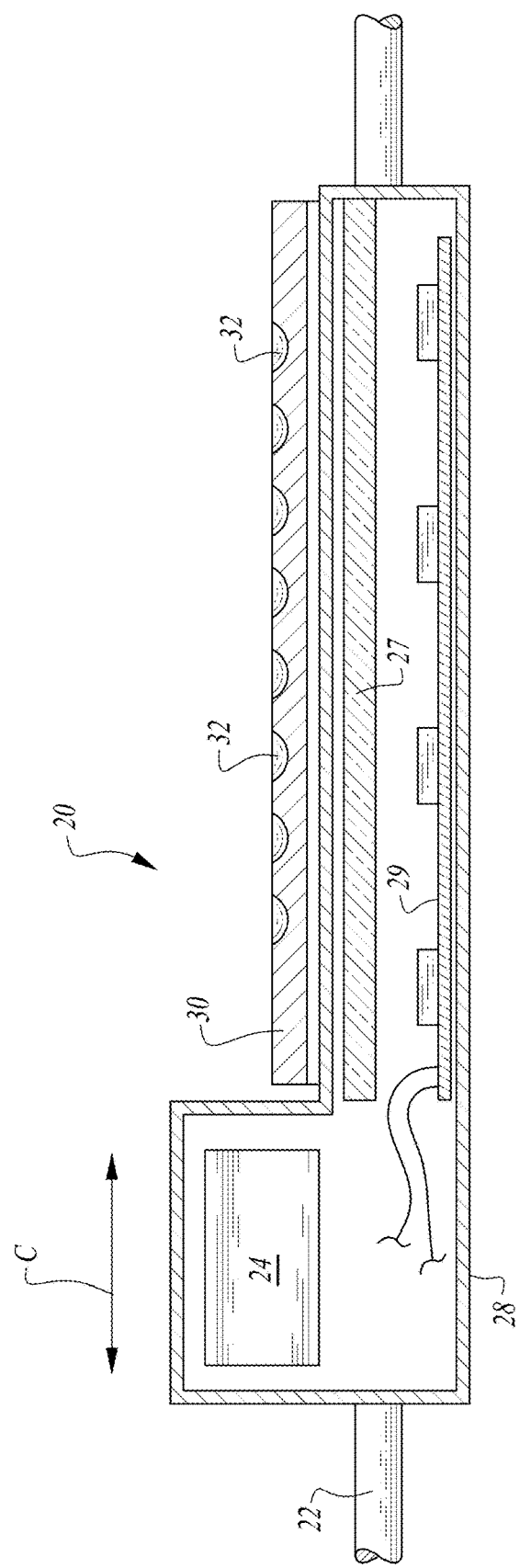
FIG. 4 is a full sectional side elevation view of the shaker assembly of FIGS. 2 and 3 revealing interior details thereof.

In essence, and with particular reference to FIG. 1, basic details of the machine 10 are described. The machine 10 includes an enclosure with an interior generally divided into a lower portion, a mid-portion and an upper portion. The overall enclosure can be similar to that of a robotic analyzer for providing a variety of different assays and other tests in an at least partially automated fashion. A lower portion of the interior of the enclosure has at least one sample rack 12 therein. A reagent rack is also located within this lower portion of the interior of the enclosure. A midlevel of the interior of the enclosure has a shaker assembly supported therein. The shaker assembly supports at least one microtiter plate 30 thereon in a manner which facilitates shaking of the entire microtiter plate. An upper portion of the interior of the enclosure has an upper carriage therein. The upper carriage can move both laterally and forwardly and rearwardly. The upper carriage carries an automated syringe, such as a microsyringe, and a camera so that the microsyringe and the camera can access each of the wells 32 of the microtiter plate 30 and so that the microsyringe 18 can access each of the locations in the sample rack 12 and the reagent rack 14.

The machine 10 is programmed to manipulate samples and reagents through the microsyringe and the microtiter plate upon the shaker assembly to perform the agglutination test. The test is then read by the camera 40 and results for each sample, along with pictures taken from the camera can be archived within a database which is correlated with information relating to the sample and other details of the test.

More specifically, and with reference primarily to FIG. 1, the particular details of the automated RPR agglutination test as conducted by the machine 10 are described, according to this preferred embodiment disclosed herein. With adjustment, such as using different reagent and/or different shaking procedures, other agglutination tests can similarly be performed. Initially, samples to be tested are loaded into the sample rack 12 of the machine 10. This sample rack 12 preferably has multiple locations where test tubes or similar structures containing a sample can be placed. Most preferably, the machine 10 includes a barcode scanner 13 thereon and tubes or other structures containing samples can have a barcode thereon so that when the sample is loaded into the rack 12 of the machine 10, the space in the rack 12 which has been loaded with the sample has been correlated with data associated with the barcode on the sample container. The user thus does not need to keep track of which space in the rack 12 has been loaded with each sample. One such rack 12 suitable for this invention is described in U.S. Published Patent Application No. 2012/0178170, incorporated herein by reference.

A reagent rack 14 is also provided into which reagent liquid is placed. Details about one appropriate reagent are described above in the Background. Preferably, this reagent rack 14 also includes a cleaning reservoir containing a cleaning solution for cleaning of the microsyringe or other fluid transfer device in between fluid transfer procedures.

Because the reagent typically has carbon particles within the liquid reagent which have a tendency to settle and detrimentally affect the quality of the reagent taken up by the microsyringe during operation of the procedure of this invention, the reagent rack 14 preferably includes a stirrer associated therewith to keep the carbon particles in suspension. In one embodiment this stirrer is a magnetic stirrer. Such a stirrer can have an impeller contained within the reagent fluid itself and which is caused to spin and keep the reagent stirred by an adjacent rotating magnetic field such as that provided by an electromagnet beneath the reagent rack 14. Other forms of stirrers could be utilized including mechanical stirrers or stirrers which repeatedly aspirate and dispense reagent sufficiently rapidly to keep the carbon products within the reagent suspended.

The microtiter plate 30 (or other well supporting structure) is loaded onto the shaker assembly 20. The microtiter plate 30 includes a plurality of wells 32 or other spaces (or at least one space in a simplest embodiment) thereon which can receive samples and reagents. In one embodiment, the plate 30 has forty-eight wells arranged in a 6×8 array. In one embodiment each well is circular with a flat or concave bottom of up to about 15 millimeters in diameter. In such an embodiment, the assembly 20 has an eccentric mass offset from a vertically oriented rotating output shaft of a motor by between about 5 millimeters and 15 millimeters (most preferably about 10 millimeters) so that an amplitude of the rotation is between about 5 millimeters and 15 millimeters (most preferably 10 millimeters). The shaker assembly 20 is configured so that it can shake such as by rotating the microtiter plate 30 at 100 RPMs. Preferably, multiple wells 32 are located on the microtiter plate 30 so that multiple samples and reagents can undergo reactions on the common microtiter plate 30 and be shaken by the common shaker assembly 20.

An automated microsyringe 18 or other fluid aspirator and dispenser gathers a sample and reagent and deposits the combined sample and reagent onto a well 32 or space on the microtiter plate 30. Most preferably, this microsyringe 18 is carried upon an upper carriage 16 which can move over the various different samples on the sample rack 12 and can also move over the reagent rack 14. The microsyringe 18 will typically first gather a predefined quantity of reagent and then further gather a predefined amount of sample and then carry both the reagent and sample to a well 32 on the microtiter plate 30 for dispensing thereon. The microsyringe 18 or other fluid transfer device could then pass to a cleaning reservoir such as adjacent the reagent rack 14 to undergo a cleaning procedure and then can gather further reagent and sample from another location on the sample rack 12 and deposit them onto another well 32 on the microtiter plate 30 located on the shaker assembly 20; and so on essentially ad infinitum.

The microtiter plate 30 undergoes shaking through action of the shaker assembly 20. The elapsed time is also tracked for each well 32 that has been loaded with a sample and reagent. After an amount of elapsed time and shaking called for by the testing protocol has been achieved, a camera 40 is aligned with the well 32 of the microtiter plate 30 which has the sample and reagent thereon and a photograph is taken of the well 32. The shaker assembly 20 preferably includes a light diffuser plate 27 beneath the microtiter plate 30 and the microtiter plate 30 (or other well support structure) is preferably formed of a transparent or translucent material to allow light to travel up through the microtiter plate 30.

An LED board 29 with a plurality of light emitting diodes surface mounted on a printed circuit board is preferably contained within the shaker assembly 20 beneath the diffuser 27 and supplied with power so that light from the LED board 29 shines up through the diffuser 27 and up through the microtiter plate 30. A backlit photograph is thus taken by the camera 40 from above looking down on the well 32 of the microtiter plate 30.

The LEDs are selected to minimize heat generation and are well ventilated to keep heat from transferring up to the microtiter plate 30. A fan can also optionally be provided to keep temperature substantially constant and at a desired temperature.

The photograph taken by the camera 40 is read to determine whether agglutination has occurred or not, and whether a positive or negative test is to be indicated. In one embodiment the reading of the photograph occurs by a trained professional. In other embodiments software might be employed to evaluate the image taken by the camera 40 with the software program automatically determining whether or not a positive test is indicated.

The photograph and/or the result of reading the photograph can be archived in a database also containing information such as that associated with the barcode on the sample container, and other information such as the date of the test, lot numbers or the reagent, and any other pertinent information (e.g. temperature at time of test, humidity at time of test, atmospheric pressure at time of test, etc.).

After all the wells 32 in the microtiter plate 30 have been utilized (or otherwise the plate 30 is no longer needed), the microtiter plate 30 can be disposed of or potentially sanitized for reuse. In addition to the basic procedure identified above, with many RPR tests it is desirable to re-perform the tests multiple times at different reagent and/or sample dilution levels. This series of titers can be selected as desired for the parameters of the RPR tests to be conducted. In one embodiment, dilution of the reagent can occur by including a diluting solution in the reagent rack 14 and having the microsyringe 18 or other automated fluid transport device take up both a predetermined amount of reagent and a predetermined amount of diluting solution, and then gathering a predetermined amount of sample from the sample location on the sample rack before transferring the combined gathered liquids to a well 32 or other location on the microtiter plate 30.

With particular reference to FIGS. 1-4, further details of the machine 10 for performing the process of this invention are described according to one embodiment of this invention. The machine 10 is generally in the form of an enclosure which includes a lower level, midlevel or upper level. The sample racks 12 preferably reside at the lower level and also a reagent rack 14. The midlevel of the enclosure is configured with the shaker assembly 20 riding upon rails 22 to allow the shaker assembly 20 to move forward and backward within the enclosure at a midlevel above the sample racks 12 and the reagent rack 14. An upper level of the enclosure includes the upper carriage 16 which rides on a bar which spans the enclosure laterally and can also be carried forwardly and rearwardly within the enclosure. A cover can isolate the entire enclosure, which pivots on a rear hinge. Such a cover is omitted in FIG. 1 to most clearly show the interior details of the machine 10.

The camera 40 and the automated microsyringe 18 (or other fluid aspirator and dispenser) are carried upon the upper carriage 16 in a manner which allows the camera 40 and automated microsyringe 18 to move laterally upon the upper carriage (along arrow A of FIG. 1). The upper carriage itself can move front to back (along arrow B of FIG. 1). Both the camera 40 and automated microsyringe 18 thus have access to be placed directly over each of the wells 32 within the microtiter plates 30 located upon the shaker assembly 20 and the microsyringe has access to each of the sample containers within the sample rack 12 and each of the reagent containers within the reagent rack 14.

The shaker assembly 20 is configured so that it can move front to back (along arrow C of FIG. 1). The automated microsyringe is configured so that it can move up and down (along arrow D) such as to access samples located within the sample rack 12 or to access reagents or diluting agents contained within the reagent rack 14.

The enclosure preferably includes the barcode scanner 13 built thereinto so that when the sample rack 12 is configured to hold tubes of samples, a barcode sticker can be placed on an exterior of the tube or other sample holder and the tube can first have its associated barcode scanned by the barcode scanner 13 before the tube is placed into one of the locations within the sample rack 12. The sample rack 12 is "intelligent" in that it can recognize when a tube has been placed therein. The rack 12 thus associates the recently loaded location in the rack 12 with the most recently scanned barcode so that a user does not need to place the test tube into a particular location, but the system automatically records where the sample test tube has been located within the sample rack 12. In this manner, an operator can load samples into the sample rack 12 by first passing tubes containing samples past the barcode scanner 13 and then placing them into a vacant location on the sample rack 12.

During this procedure, the shaker assembly 20 is typically located at a rear of the enclosure. If a large number of samples are being stored on the sample rack, 12 a rear lower portion of the enclosure can have portions of the sample rack 12 located there and the shaker assembly 20 can move to a forward location so that an operator can access locations within the sample rack 12 rear area. Reagent materials are supplied into appropriate reagent locations on the reagent rack 14 when the shaker assembly 20 is in a forward position (moving forward along arrow C of FIG. 1) so that the reagent rack 14 can be accessed. Software and/or sensors can be employed to prevent collisions, such as between the microsyringe 18 and the shaker assembly 20.

At least one microtiter plate 30 is loaded onto the shaker assembly 20. The shaker assembly 20 is configured so that four "6×8" microtiter plates 30 can be provided thereon which each include forty-eight wells 32. A magnetic stirrer or other stirrer associated with the reagent rack 14 is activated to keep carbon particles within the reagent in suspension. The machine 10 is now ready to automatically perform the RPR assay test according to particular design protocols for the test to be conducted.

First, the upper carriage 16 is positioned so that the automated microsyringe 18 can access the reagent container on the reagent rack 14. Any dilution fluid is also gathered from the reagent rack 14. Next, the automated microsyringe 18 moves upon the upper carriage 16 and the upper carriage 16 moves itself (along arrows A and B of FIG. 1) to place the automated microsyringe 18 over the appropriate location on the sample rack 12 to gather a portion of one of the samples into the microsyringe 18. A portion of the sample is then aspirated. The microsyringe 18 is then elevated (along arrow D of FIG. 1) and through a combination of movement of the upper carriage 16 and the shaker assembly 20 (along arrows A, B and C) the automated microsyringe is placed over one of the wells 32 on one of the microtiter plates 30 resting on the shaker assembly 20. The automated microsyringe 18 then is moved down over the well 32 (along arrow D of FIG. 1) and caused to dispense the sample, reagent and any diluting agent into the well 32.

A shaker motor 24 is activated and the shaker assembly 20 is caused to shake the microtiter plate 30. The shaker motor 24 is preferably coupled to an eccentric 26 weight or weights, or coupled to a belt that is unbalanced or other known shaker elements are utilized to perform the desired shaking. The machine 10 keeps track of the time that the reagent and sample came into contact or were dispensed into the well 32. Multiple times for multiple wells 32 can be simultaneously tracked. The shaker assembly 20, and upper carriage 16 and automated microsyringe 18 can repeat the above process to gather further reagent and further sample, typically after a self-cleaning procedure for the microsyringe 18 is conducted. In this way, a second sample and reagent combination can be dispensed onto a second well 32 on the microtiter plate 30.

Typically, the shaker motor 24 will stop briefly during this dispensing process and then recommence shaking. Any movement of the shaker assembly 20 front to back (along arrow C of FIGS. 1 and 3) is sufficiently slow that it does not interrupt the shaking procedure for the specimen and reagent. This process can be continued potentially for as many tests as there are samples stored on the sample rack 12 and for the number of wells 32 available on the microtiter plates 30 on the shaker assembly 20.

After the predetermined amount of time for the assay has elapsed, the upper carriage 16 is moved appropriately to position the camera 40 over wells 32 for which the time has elapsed. The shaker assembly 20 is typically briefly stopped while a photograph is taken with the camera 40. Before this photograph is taken, the LED board 29 is energized so that light emitting from the LED board passes through the diffuser 27 and through the transparent or translucent microtiter plate 30 for backlighting of the photograph. The shaker assembly 20 can then recommence the shaking procedure.

An image file is created by the camera 40 and this image file is archived. The image file can also be transmitted to a display for viewing by a trained operator so that the photograph can be read to determine what the result of the test is. Alternatively, the reading of the test can be automated. Test results can be added to this archive data file.

When all of the wells 32 on all of the microtiter plates 30 have been read the microtiter plates 30 that have been fully utilized can be removed from the shaker assembly 20 and disposed of or washed and sanitized for reuse. New (or cleaned) microtiter plates 30 can be loaded onto the shaker assembly 20. Sample containers can be removed from the sample rack 12 and new samples loaded into the sample rack 12, and additional reagent can be provided into the reagent rack 14 and the entire testing procedure can continue with a new set of samples.

While the machine 10 and process are particularly defined herein for RPR tests such as a test for evaluating whether or not agglutination/flocculation has occurred when a sample is brought into contact with a reagent, other similar tests could also be performed utilizing the process and machine 10 of this invention. In particular, any tests which require combination of two or more liquids together, with or without the requirement of shaking and/or elapsed time, and which require a photograph to create an image of the liquids after any reaction has occurred, could be performed utilizing the machine 10 and process of this invention.

Utilizing the equipment described above, as well as the process described above, a sample within the well or other sample containing space has a generally circular form and charcoal or other contrast agents have been arranged in the form of a ring within the well. The ring is evaluated to determine whether agglutination has occurred or not, indicative of the sample being reactive or non-reactive. In particular, if the ring is smooth and uniform, no agglutination/flocculation has taken place and the sample is non-reactive. If the ring is broken up into clumps of contrasting agent this is indicative of a reactive sample where agglutination has taken place. In a simplest embodiment, evaluation of the sample could merely involve visual inspection of the sample by the human eye and drawing a conclusion as to whether the ring is smooth or clumped and in turn whether the sample is non-reactive or reactive. As a modification of such a simple embodiment, a camera can be utilized to take an image of the specimen and then this image can be evaluated by a human evaluator, either located at the same location where the sample is located or at some remote location (by transmitting the image to the remote location for viewing by the evaluator).

Most preferably according to a preferred form of this invention, an image is taken of the sample and then the image is evaluated in an automated fashion with an automated result outputted as to whether the sample is reactive or non-reactive. To execute such an automated process, an image is first taken by a camera, which is most preferably a digital image (but could be a non-digital image and then such a non-digital image could then be later digitized). The digital image undergoes preprocessing, including centering of the image on a center of the sample containment area, such as a well of a microtiter plate located in a middle of the image, compensating for non-uniform background illumination within the image, and masking zones of non-interest in black, such as four corners of the image which would typically be a square or rectangular image, so that a generally circular area of the well or other sample containment space is all that remains unmasked.

Some examples of sample images after this pre-processing has occurred are shown in FIGS. 6-17. In the case of non-reactive samples, the charcoal typically occurs in a smooth dark ring in the center of the image. There are also cases in which no ring forms. In the case of reactive samples, agglutination of the charcoal may retain at least a somewhat ring-like shape, but the particles are well defined and clumped into larger separate regions that can occur all over the image, and more dispersed from the ring. The goal of the software interpretation algorithm is to identify any ring shaped pattern that occurs in the image and detect particle agglutination in the area around the ring (for a reactive sample) or a smooth uniform ring (for a non-reactive sample).

A series of steps are then performed upon the remaining image of the sample to determine whether the sample is reactive or non-reactive. These steps are numbered sequentially and are provided as follows:

Step 1: Two concentric circles are added to the digital image which are strategically selected to have radii which cause the ring of contrasting agent within the sample to be bounded between the two concentric circles. Sizing of these two concentric circles involves knowing or determining the pixel size of the image and a typical radius of the ring of contrasting agent (typically by prior experience), and then selecting radii for an outer circle and an inner circle to add to the image which are sufficiently greater and lesser in radius to the ring of contrasting agent so that the ring of contrasting agent is contained between the two circles added to the image. In one example (FIG. 18) where the image is known to be 800×800 pixels, an inner circle of radius 160 pixels is provided and an outer circle of radius 280 pixels is provided.

Step 2: 360 radial lines (or some other number of lines selected by an operator) are drawn between the inner circle and the outer circle of Step 1. In the example provided above, these lines are each approximately 120 pixels long and separated circumferentially by one degree of spacing. This step is depicted in FIG. 19 with the inner and outer circles shown in red and the radial lines shown in blue. These lines are shown in FIGS. 13 and 14 to depict how the sample image is being evaluated, but do not need to be actually physically drawn in a visually perceptible manner to practice this invention.

Step 3: For each of the radial lines (360 in the example above) a darkest pixel along each of the radial lines is identified. This darkest pixel is determined by taking an average of the darkness of the eight pixels that surround each pixel. The darkest pixel identified along each of these radial lines is then plotted in a cartesian graph with an X coordinate representing the number of the radial line (between number 1 and number 360 in the example provided above) and with the Y coordinate being the position of the darkest pixel along the radial line which is the darkest. For instance, if the darkest pixel is 55 pixels away from the inner circle it would have a value of 55. All of these points are plotted on this cartesian coordinate graph (see blue dots in FIG. 20).

Step 4: A polynomial curve is fitted to these data points in the cartesian coordinate graph (red line in FIG. 20). This curve is fit utilizing at least a fourth order polynomial curve being fitted to the data points, but most preferably is a sixth order (or possibly higher order) polynomial curve that is fitted to the data points. This polynomial curve that is fitted to the data points is also drawn on the same cartesian coordinate graph along with the raw data, with this curve being represented in a contrasting color or some other contrasting manner so that it can be distinguished from the raw data.

Step 5: Data points on the graph which lie further than 20 pixels (or some other "out lyer" setting amount) from the polynomial curve are deleted from the data set. For instance, the three blue dots off of the main curve (at about radial lines 50, 110 and 202) can thus be deleted.

Step 6: After these out lyer data points have been removed from the data set, a new polynomial curve is fitted to the remaining data points, preferably with another sixth order polynomial curve. If desired, the curve fitted to the data in Step 6 can be drawn in a circular coordinate graph overlaid upon the image itself, and with such an overlay of the fitted curve in circular coordinates overlaid upon the image causing this fitted curve to closely approximate the position of the ring in the image. FIG. 21 shows such a curve in red overlying the sample image.

Such an overlay can be visually displayed and reviewed by an operator as a visual check that the first six steps of the process have been accurately performed and a mathematical curve has been fitted to the data associated with the ring of contrast material. One will recognize that if the sample is non-reactive, the fitted curve will have an appearance and form which closely follow the ring of contrast material in the image. However, if the sample is reactive and agglutinated, the contrasting agent will be clumped together along a generally ring-like path, so that the fitted curve will be smooth and continuous, while the actual contrasting agent in the image will be clumped together. However, the fitted curve will tend to intersect the locations of the clumps (or follow a line which generally is an average distance from a center of the image as the fitted curve extends circularly about a center of the image).

Step 7: The image is further analyzed by dividing the image adjacent to the curve with 720 radial lines substantially perpendicular to the curve, each radial line of a length 30 pixels long and spaced apart every 0.5 degrees along the fitted polynomial curve. FIG. 22 depicts this step with the curve shown in red and the 720 radial lines shown in yellow. This yellow region is not a perfect circle, but follows the ring in the image. The radial lines are located perpendicular to the polynomial curve and positioned so that 10 pixels of each radial line lay between this curve and the center of the image and 20 pixels of the radial line lay between the curve and the outside of the image. These 30 pixels of each of these 720 radial lines are further evaluated to determine whether or not agglutination has taken place.

Step 8: The darkness of each pixel along each radial line is calculated. The darkness of each pixel is determined to be an average of the 8 pixels surrounding each pixel, similar to the process utilized in Step 3. In addition to the darkness of each pixel, a coefficient of variation (CV) of the darkness of the pixels along each of the 720 radial lines is calculated. If a radial line crosses an area with a significant amount of darkness variation, the CV for that radial line will be high. These CVs are displayed as a dashed line histogram to provide what is referred to as "Ring Ray CV" values, depicted in FIG. 23 overlying a portion of the sample image. 720 such values are provided, with each CV value plotted in a Y direction in cartesian coordinates while the number of the radial line (between 1 and 720) is plotted in the X direction within the cartesian graph. Greater variation in darkness levels along each radial line produces a higher CV value and little or no variation along a radial line provides a low CV value. Different CV values for a radial lines might occur where a radial line follows a path which passes between clumps of contrast material, rather than where a radial line passes through a clump of contrast material.

Step 9: The progressive average over a series of 15 points on the Ring Ray CV histogram are calculated. That is, for each value on the Ring Ray CV histogram, an average value of the previous seven values and the following seven values is calculated. These averages will be highest at centers of clumps of contrasting material, while a non-reactive specimen without appreciable clumping will have corresponding averages which remain substantially uniform. An indication of agglutination is thus provided.

Figure 24:
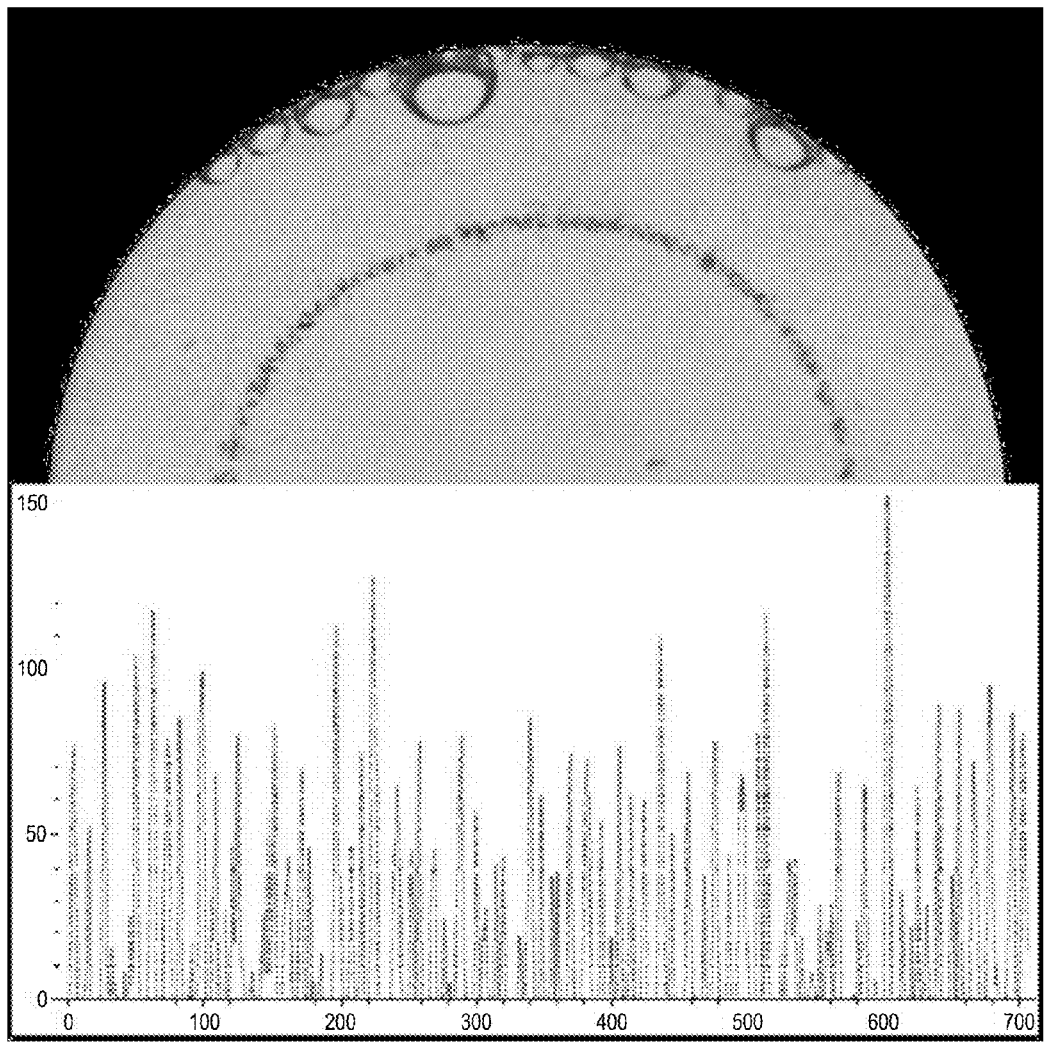
FIG. 24 is a histogram overlaid upon the photograph of the sample shown in FIG. 7, with the histogram plotting a difference between an average of adjacent CV values and the actual CV value for each radial line upon the image of FIG. 22, as a measure of "bumpiness" of the regions of contrasting agent concentration.

Step 10: The difference of each value on the Ring Ray CV histogram (FIG. 23) and the progressive average at the same location (Step 9) is calculated. These differences reflect how "bumpy" the Ring Ray CV histogram is (and generally indicative of clumping and agglutination in the sample). These differences can be visualized as an option, and appear as a histogram (see FIG. 24). Higher peaks in this histogram indicate more deviation with the local average. This histogram can be known as the ring ray delta CV values histogram. The heights of the peaks of the "Ring Ray Delta CV" histogram are stored in six bins. Bin 1 is the number of the peaks with a height between 1 and 11. Bin 2 is the number of the peaks with a height between 12 and 23. Bin 3 is the number of the peaks with a height between 24 and 44. Bin 4 is the number of the peaks with a height between 45 and 88. Bin 5 is the number of the peaks with a height between 89 and 176. Bin 6 is the number of the peaks with a height above 176. The number of peaks in each bin thus correlates with the uniformity of the ring and thus correlates with whether or not agglutination has occurred within the sample. While six bins are identified, and provided in a preferred embodiment of this invention, a smaller or greater number of such bins could be utilized (and with different boundaries for each bin) and still exhibit some effectiveness according to the process of this invention. Preferably at least three bins are provided as a minimum, and preferably no more than about a dozen bins are provided at an upper extreme.

Figure 25:
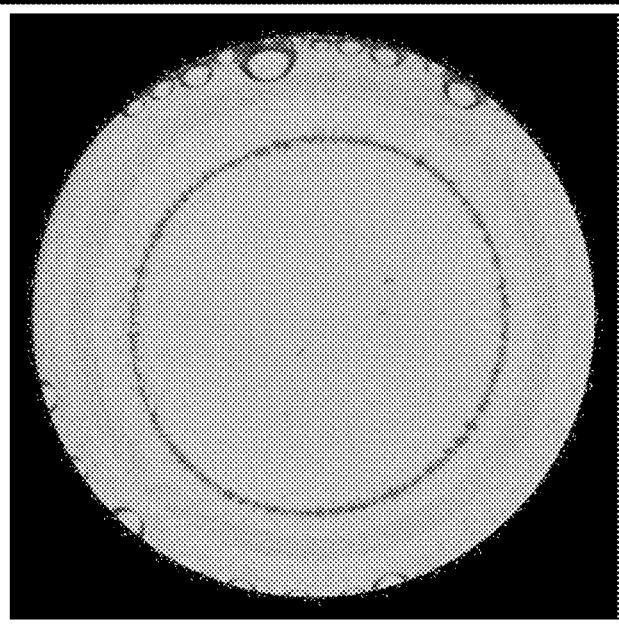
FIG. 25 shows the photograph of FIG. 7 with the fitted curve of FIGS. 20 and 21 shown in purple and with further border region radial lines (shown in green) provided to evaluate contrast agent concentration near a border of the well of the sample shown in FIG. 7.

Step 11: In some cases agglutination can happen outside of the circular area defined by the rings in Step 1. Agglutination can even occur as quite large bits in the area close to the edge of the well. In order to detect agglutination in areas of the well or other sample containment space outside of the area between the two concentric rings, similar processing as that described in Steps 7-10 is performed along an outer ring outside of the outer concentric circle of Step 1. In the example provided above in Step 1 with an 800×800 pixel image, such an outer ring includes 40 pixel long radial lines which are positioned 290 pixels from a center of the image. The CVs of the darknesses detected in this outer region are calculated. This calculation is performed similar to that described above. These values are known as the "Border Ray CV values." This Step 11 is depicted in FIG. 25 with the previous curve from Step 6 (FIG. 21) shown in purple and the border radial lines extending between the two concentric rings shown in green.

Figure 26:
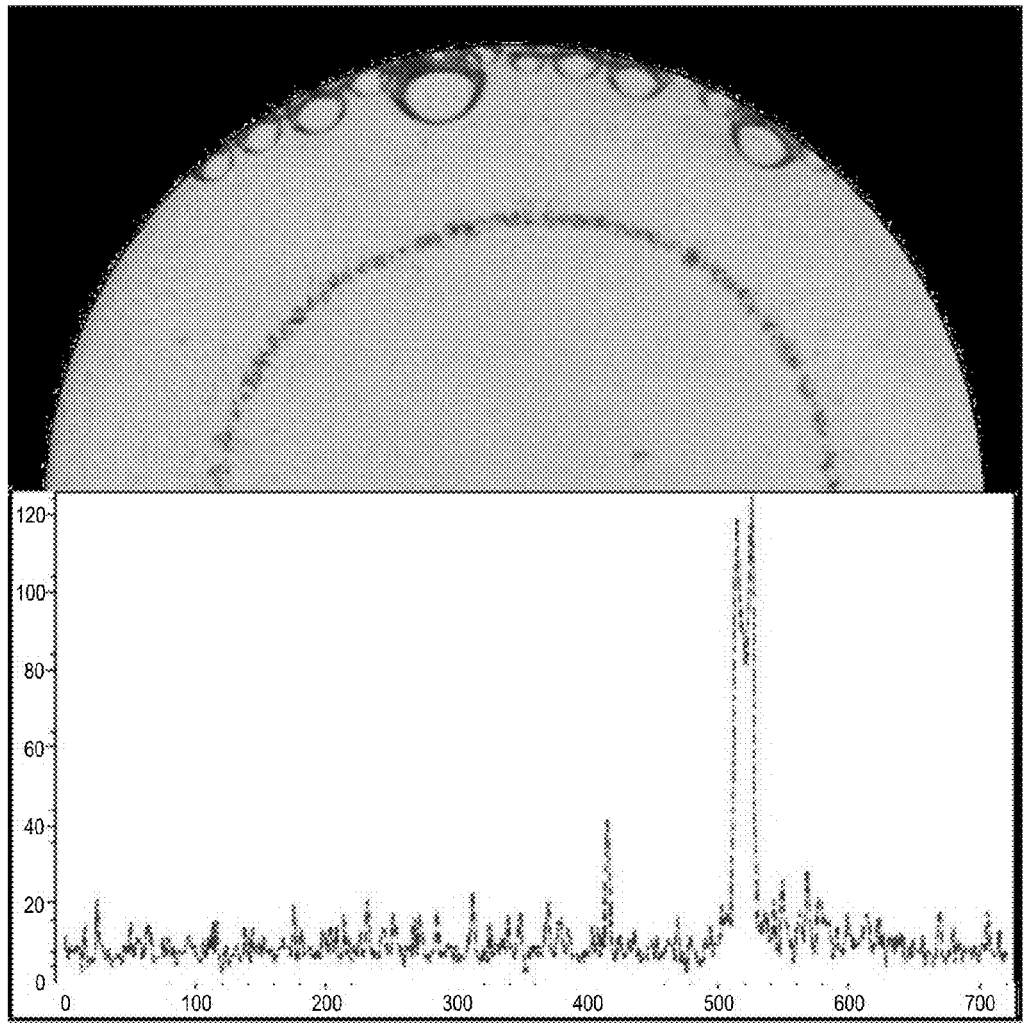
FIG. 26 shows a histogram overlying a portion of the photograph of FIG. 7, the histogram plotting a difference between border region CV values along each radial line of FIG. 25 and average of CV values for a group of adjacent radial lines, the plot shown in blue.

As is done with the Ring Ray CV values, a progressive average is calculated and the differences are used to determine agglutination in this outer region. These different values are known as the "Border Delta CV" values. These Border Delta CV values are visualizable in cartesian coordinates with 720 radial lines identifying an X coordinate for these cartesian graphs and with the Border Delta CV value for each radial line being graphed as a Y coordinate of the cartesian graph (see FIG. 26 where the histogram is overlaid upon a portion of the sample image). These values for the Border Delta CV are preferably not divided into bins as in Step 10 above for the Ring Ray Delta CV values. Instead, other characteristics of this histogram are used to determine the reactive or non-reactive nature of the image.

Figure 27:
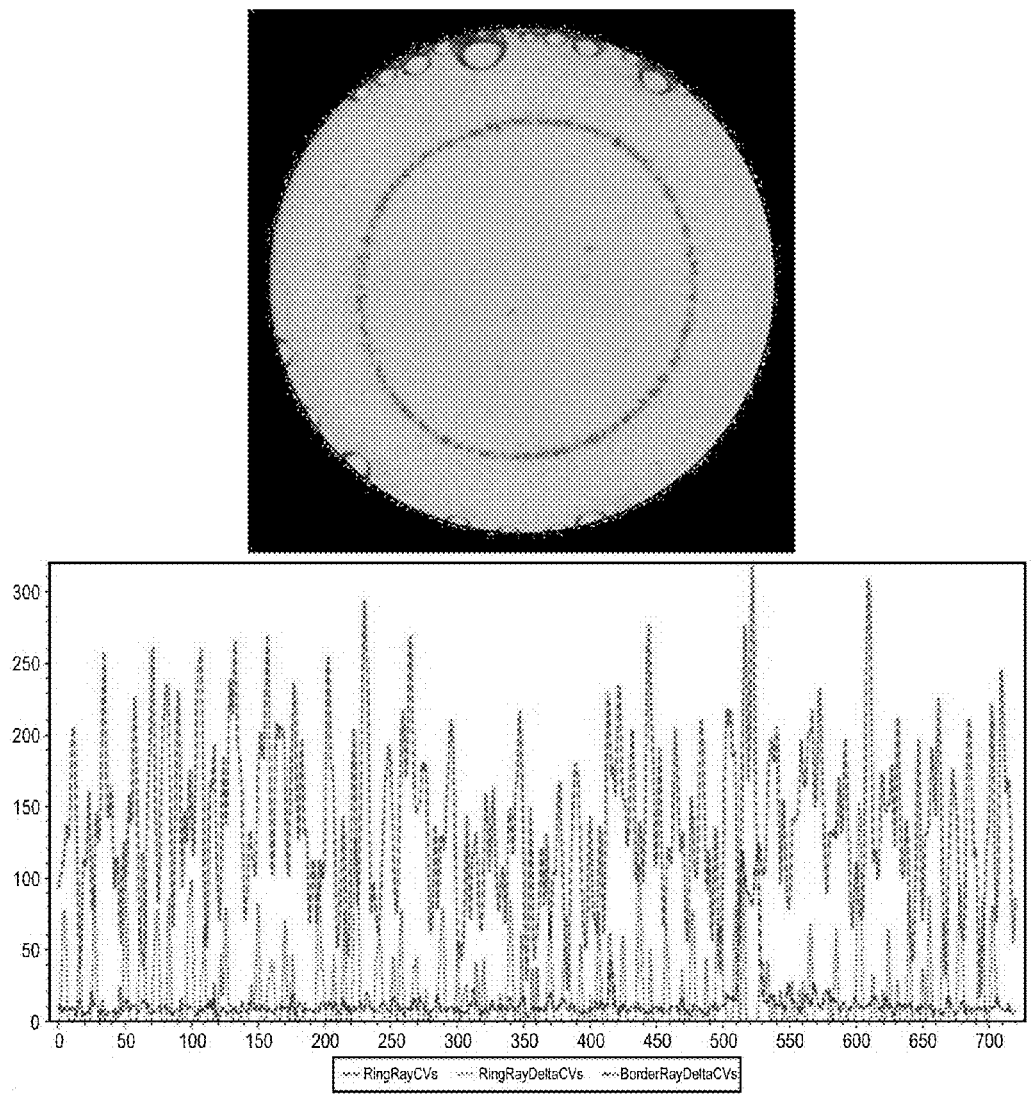
FIG. 27 shows a reproduction of the sample image of FIG. 7 above a combined histogram of data shown in FIGS. 23, 24 and 26.

Step 12: In particular, the reactive or non-reactive nature of the sample images is calculated using the information determined in Steps 1-11. FIG. 27 depicts the histograms associated with these steps all upon a common chart, and with red for the Ring Ray CV values, with green for the Ring Ray Delta CV values and blue for the Border Ray Delta CV values. A total of up to twelve parameters are passed to a detection tree algorithm which determines if the image represents a reactive or non-reactive sample based on the values of these twelve parameters. The twelve parameters used in one embodiment for the decision tree algorithm include:

1) The number of peaks in Bin 1.
2) The number of peaks in Bin 2.
3) The number of peaks in Bin 3.
4) The number of peaks in Bin 4.
5) The number of peaks in Bin 5.
6) The number of peaks in Bin 6.
7) The sum of the values in Bins 4, 5 and 6.
8) The standard deviation of the Ring Ray CV values.
9) The area under the Ring Ray CV histogram.
10) The standard deviation of the Border Ray CV values.
11) The area under the Border Ray CV histogram.
12) The maximum value of the Border Ray Delta CV values.

Figure 28:
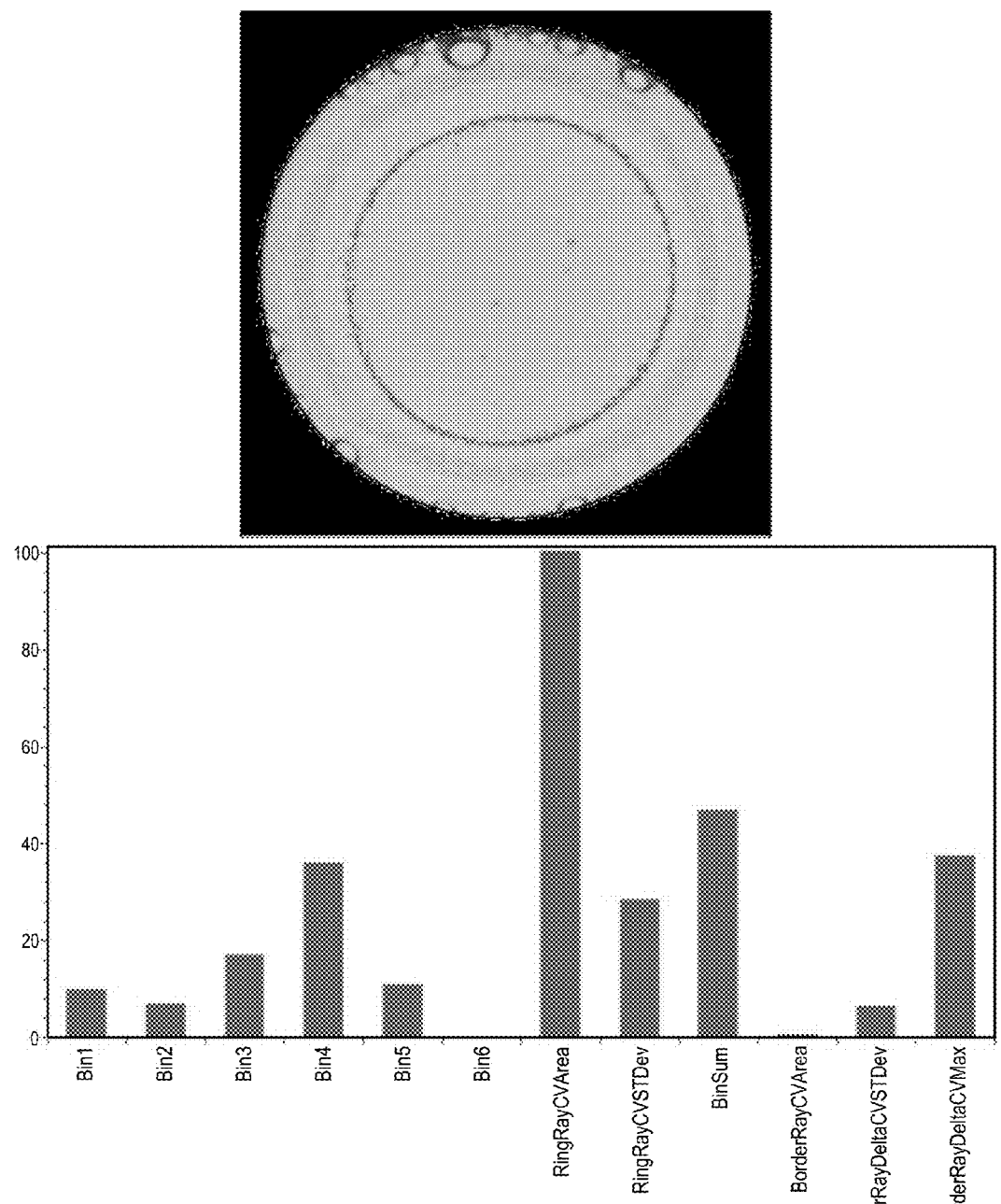
FIG. 28 shows a representation of the sample image of FIG. 7 above a bar chart of twelve parameters used to evaluate agglutination in the sample, the representation including the fitted curve of FIGS. 20 and 21 in red, the radial lines extending from the fitted curve in yellow and the border area radial lines in green.

FIG. 28 shows the image of FIG. 7 above a bar chart of these twelve parameters. The image shows the fitted curve in red, the radial lines extending from the fitted curve to form the Ring Ray CV values in yellow and the radial lines in the border area of the sample to form the Border Ray CV values in green. FIG. 28 thus aggregates meaningful information as to the presence or absence of agglutination for machine (or human) processing.

Example 1

In one embodiment, the decision tree algorithm for determining the reactive and non-reactive nature of the sample image was generated using the Accord C45 learning algorithm provided by accord-framework.net available as open source code available on GitHub. A large number of sample images having a known reactive or non-reactive status were analyzed for the twelve parameters listed above and the Accord C45 learning algorithm was also programmed with the known results associated with each of the images. The Accord C45 learning algorithm then generated a decision tree algorithm which was used to determine the reactive or non-reactive nature of other images presented according to the process of this invention. The Accord C45 learning algorithm was thus effectively trained how to call reactive images and non-reactive images from these twelve parameters.

Example 2

FIGS. 27 and 28 depict a sample image (upper portion of FIG. 27) histogram of related data from the process described above (lower portion of FIG. 27), the sample image with overlaid image processing lines superimposed thereupon, and values for the twelve parameters evaluated by the process of this invention. In the histogram, the Ring Ray CV values are depicted in red, the Ring Ray Delta CV values are depicted in green and the Border Ray Delta CV values are depicted in blue. Lines overlaid on the sample image (FIG. 28) include a red line for the curve fitted to the contrasting media in the sample, and with radial lines perpendicular to the fitted curve shown in yellow, and with the border radial lines shown in green. The results in this example was a finding that the sample was reactive.

Example 3

Figure 29:
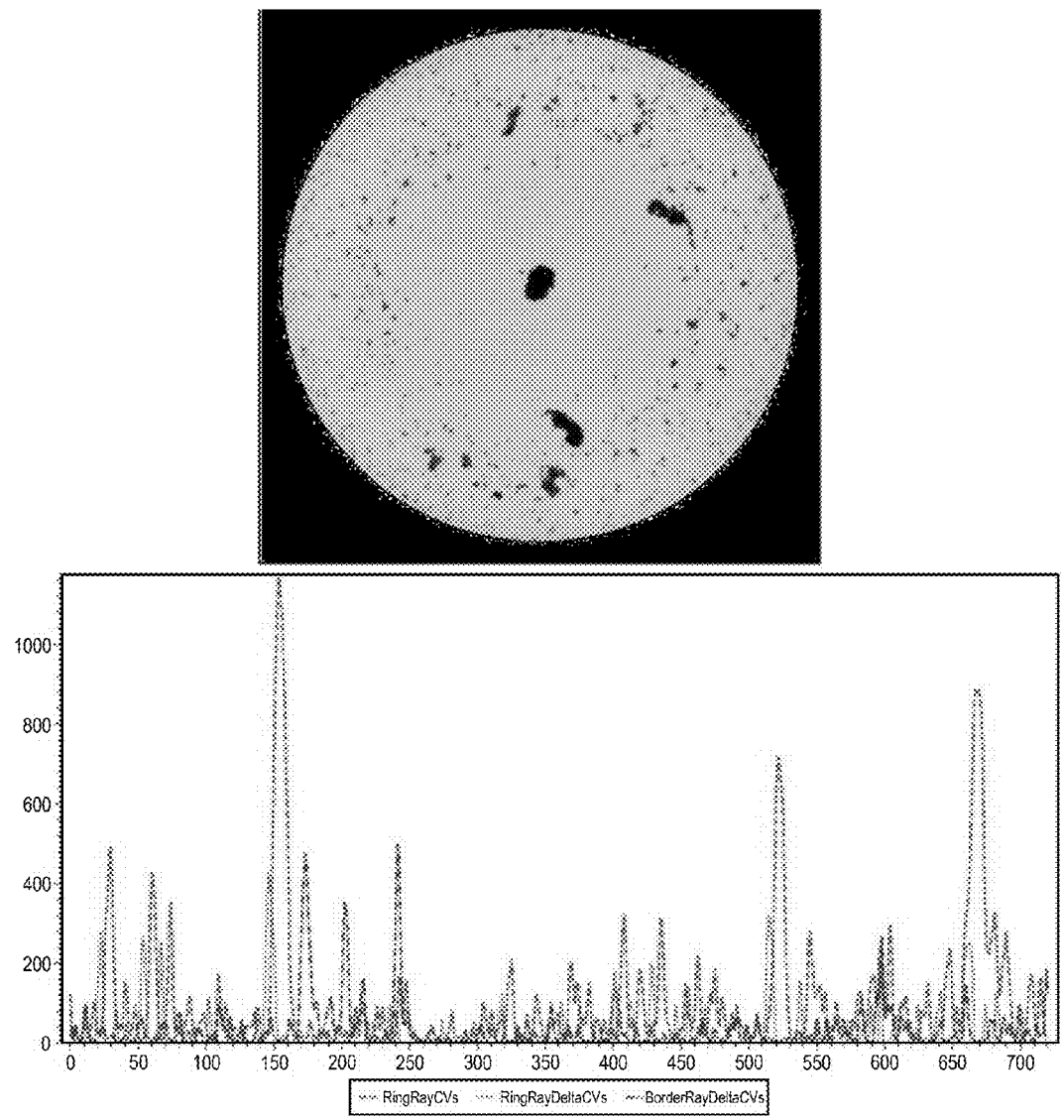
FIGS. 29 and 30 are depictions corresponding with FIGS. 27 and 28, but for a new sample.
Figure 30:
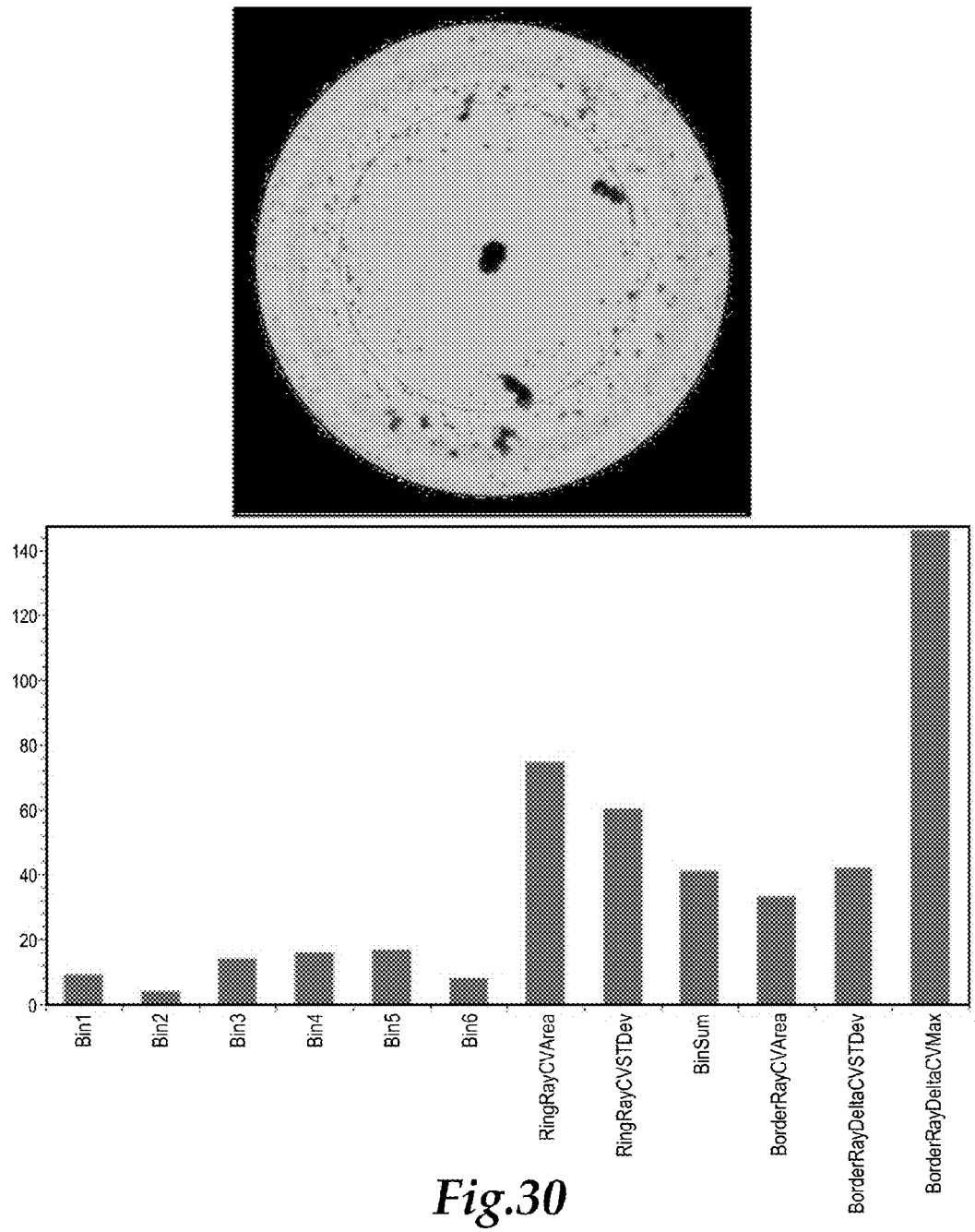

FIGS. 29 and 30 depict a further sample image (upper portion of FIG. 29) featuring a high degree of dumpiness. In this example similar colors are used for similar data in the histogram (lower portion of FIG. 29) and for the processed image and for the twelve parameters evaluated. The result of the evaluation for this sample was reactive.

Example 4

Figure 31:
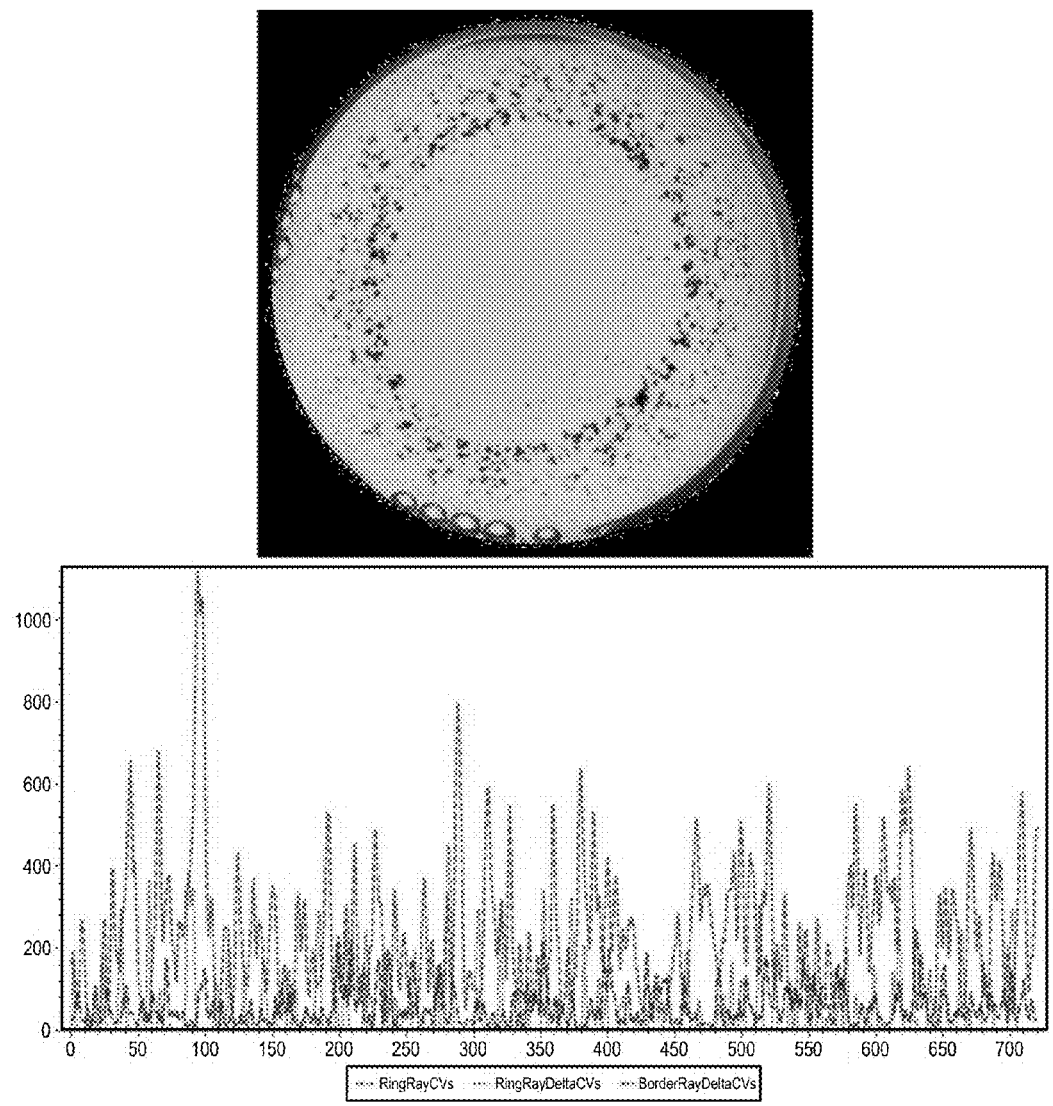
FIGS. 31 and 32 are depictions corresponding with FIGS. 27 and 28, but for a new sample.
Figure 32:
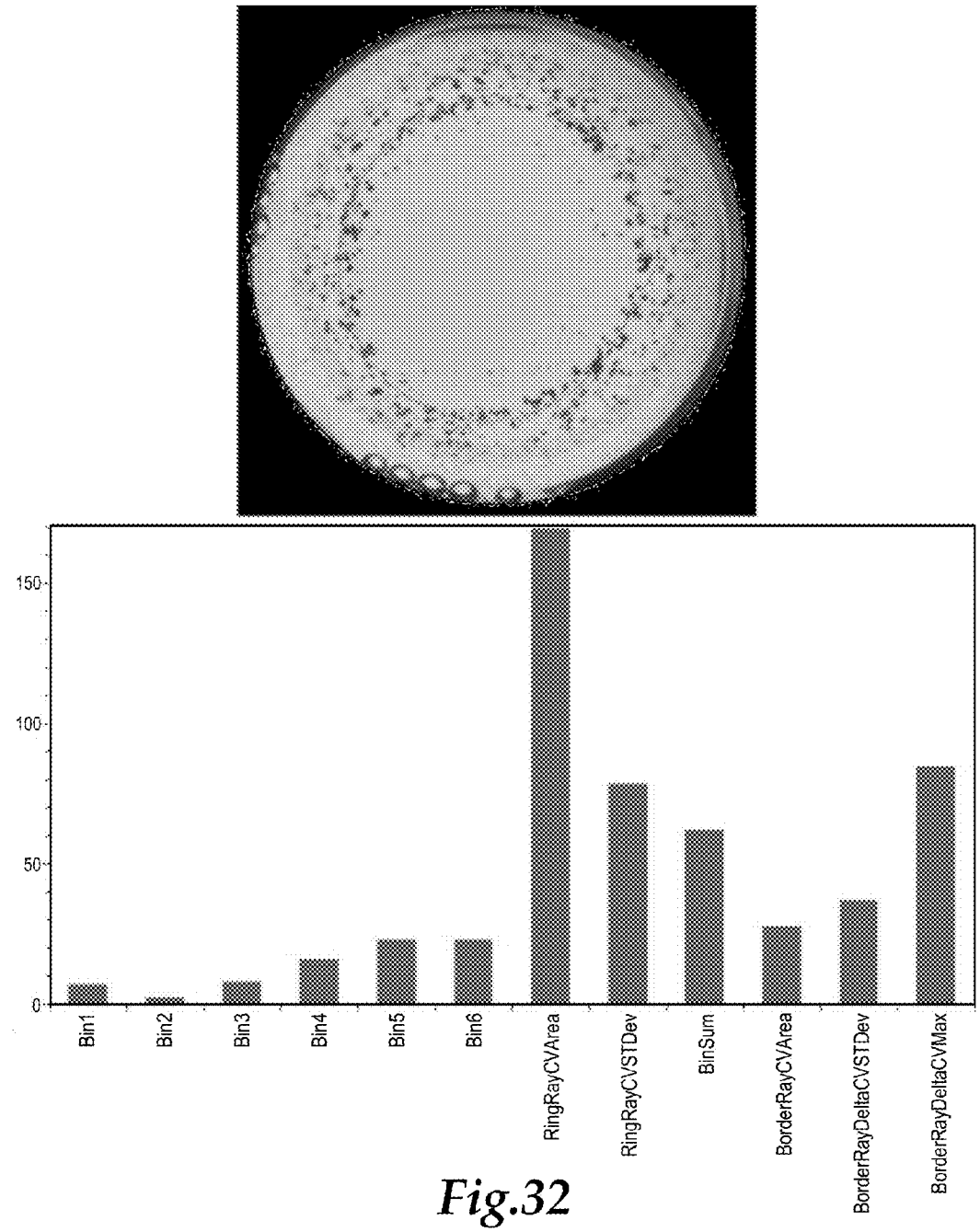

FIGS. 31 and 32 depict a further sample image (upper portion of FIG. 31) with moderate dumpiness. In this example similar colors are used for similar data in the histogram (lower portion of FIG. 31) and for the processed image and for the twelve parameters evaluated. The result of the evaluation for this sample was reactive.

Example 5

Figure 33:
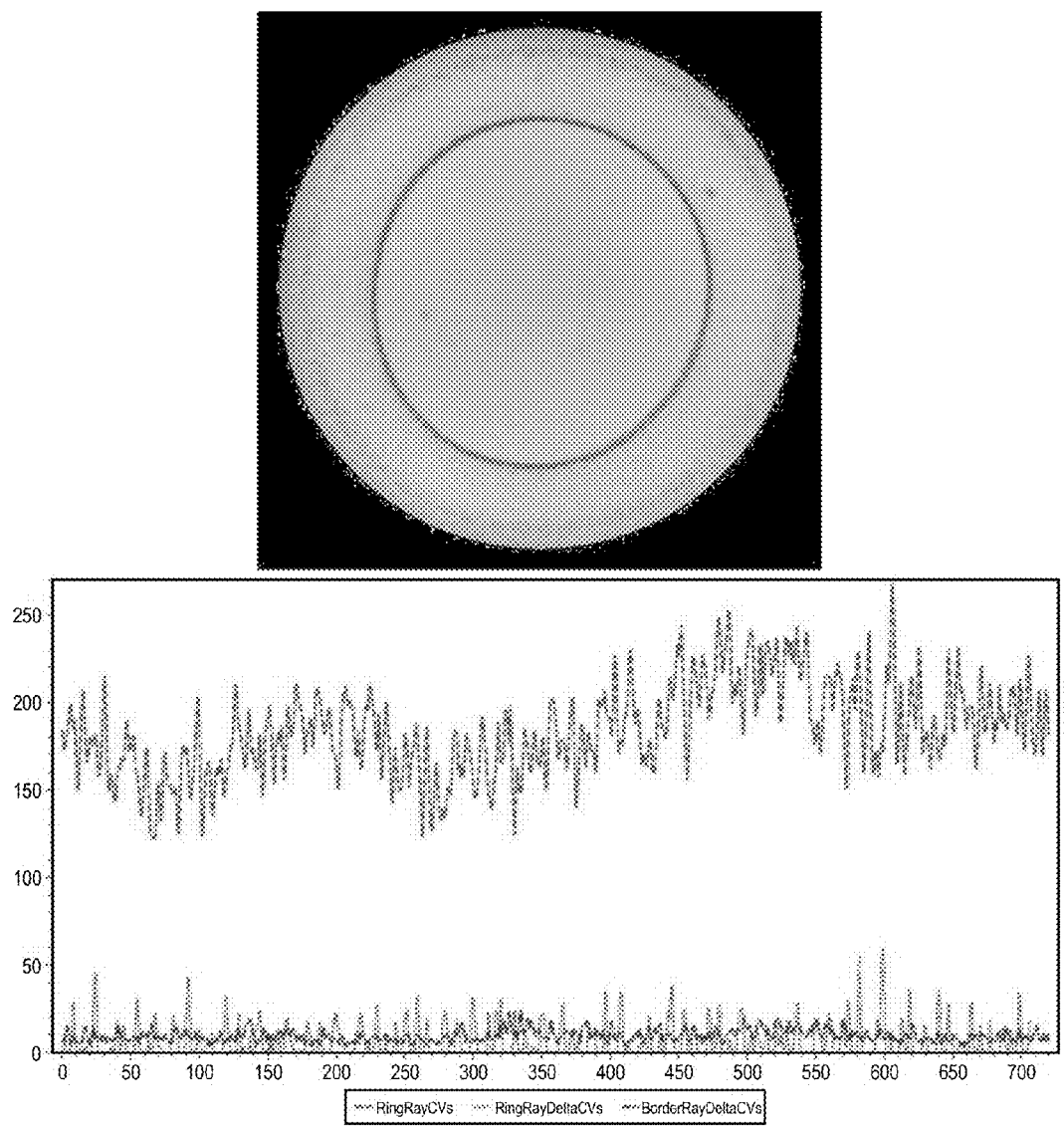
FIGS. 33 and 34 are depictions corresponding with FIGS. 27 and 28, but for a new sample.
Figure 34:
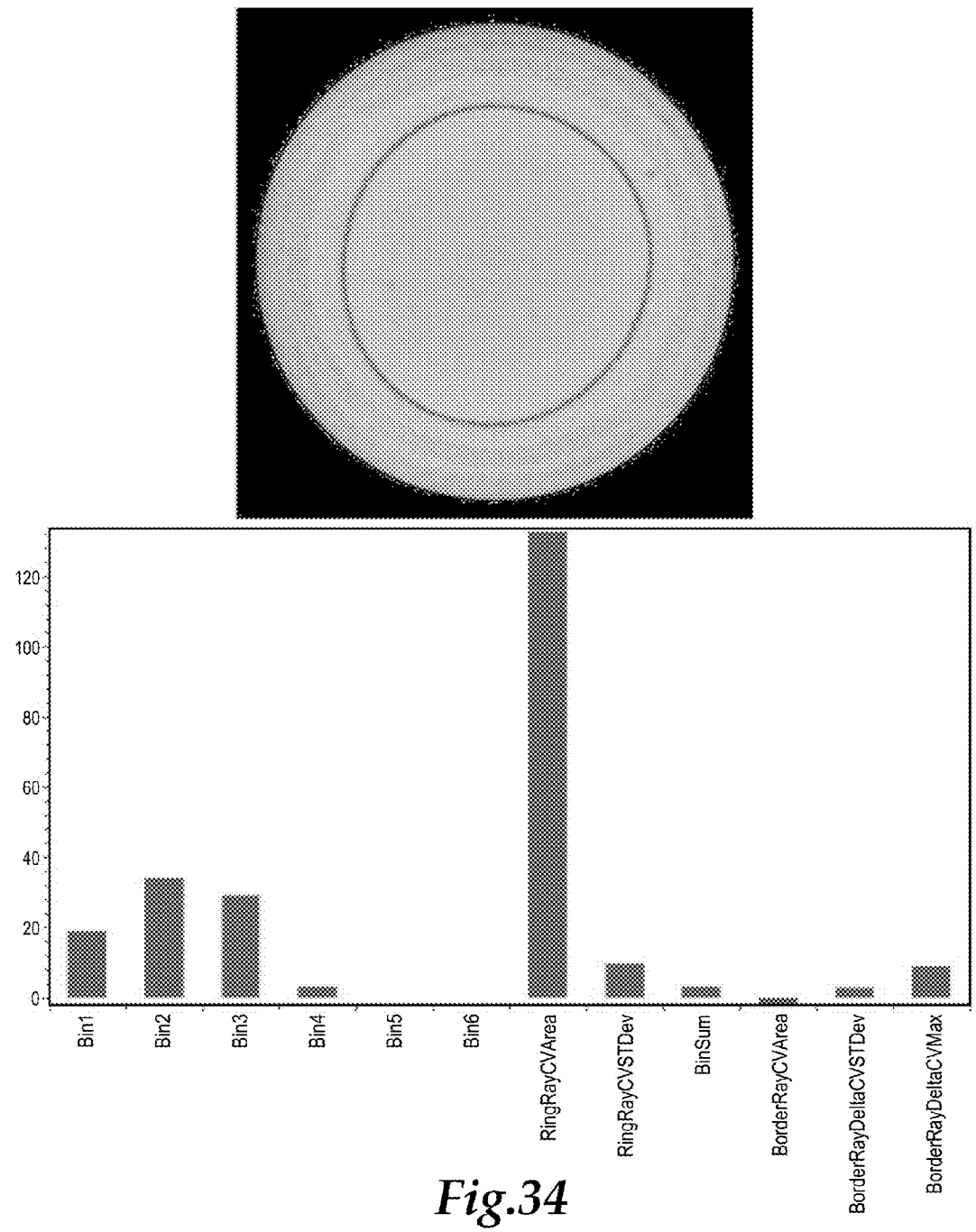

FIGS. 33 and 34 depict a further sample image (upper portion of FIG. 33) with no appreciable dumpiness. In this example similar colors are used for similar data in the histogram (lower portion of FIG. 33) and for the processed image and for the twelve parameters evaluated. The result of the evaluation for this sample was non-reactive.

Example 6

Figure 35:
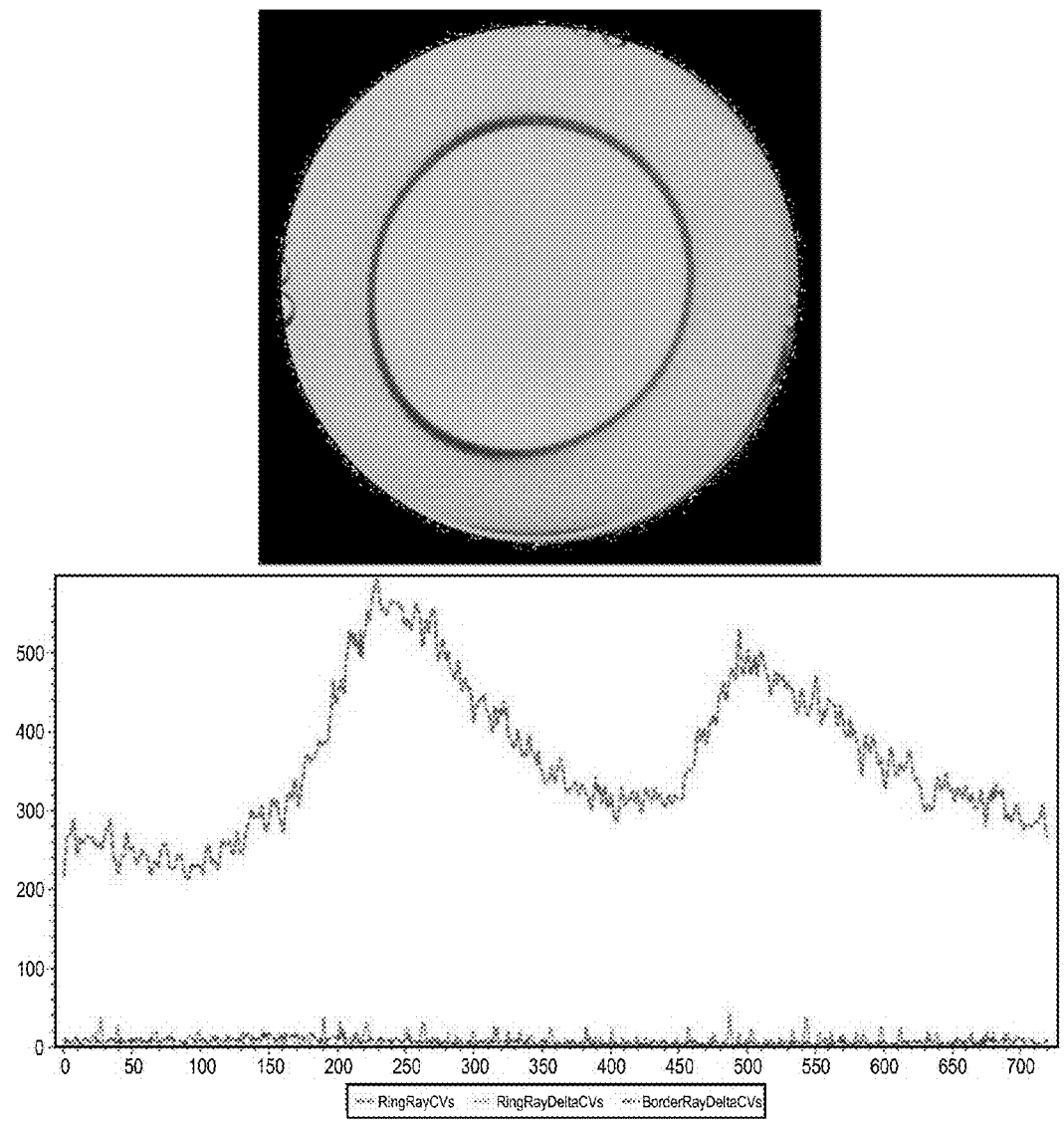
FIGS. 35 and 36 are depictions corresponding with FIGS. 27 and 28, but for a new sample.
Figure 36:
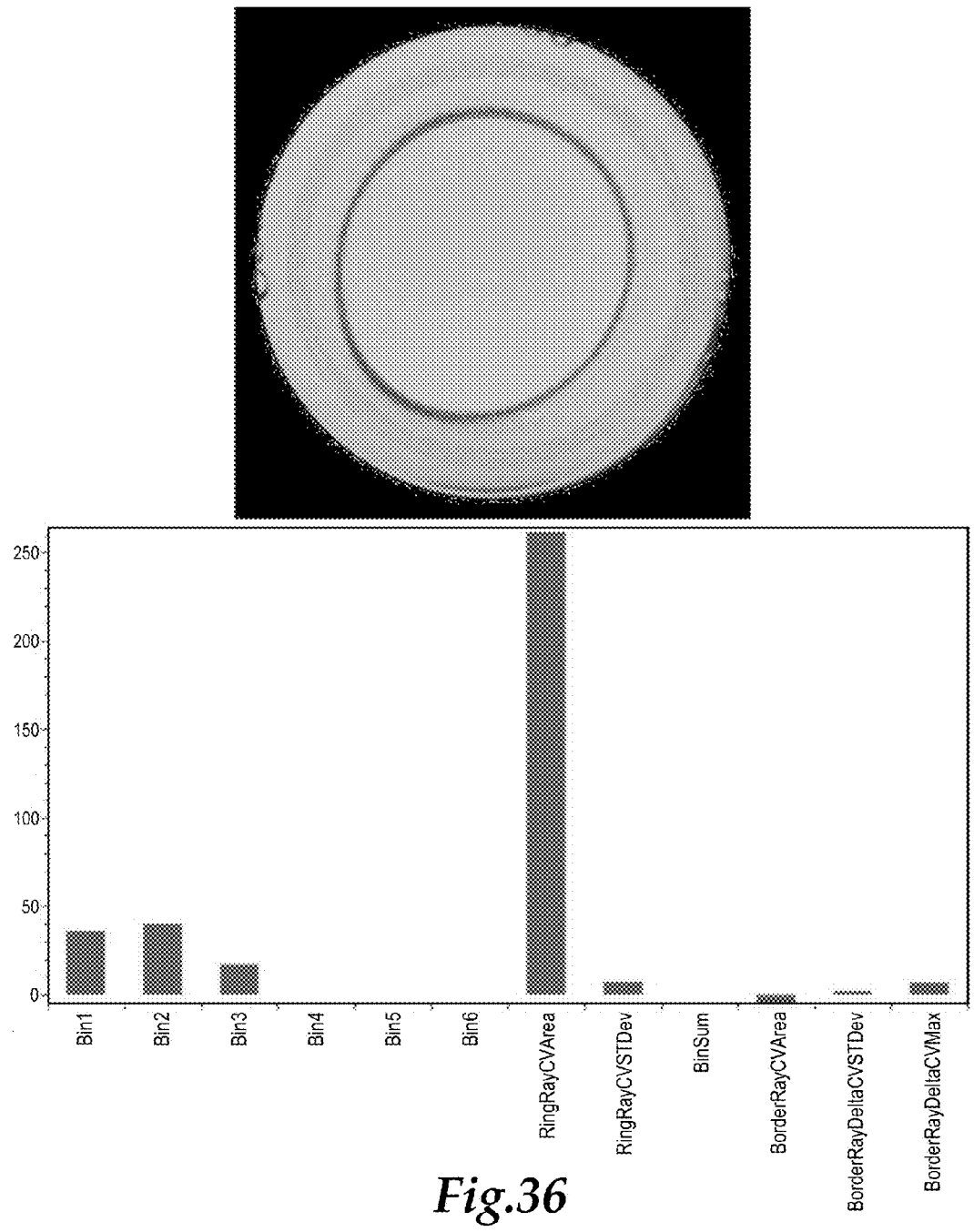

FIGS. 35 and 36 depict a further sample image (upper portion of FIG. 35) with a dark ring and no appreciable dumpiness. In this example similar colors are used for similar data in the histogram (lower portion of FIG. 35) and for the processed image and for the twelve parameters evaluated. The result of the evaluation for this sample was non-reactive.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A method for determining whether a sample is reactive or non-reactive when combined with a rapid plasma antigen reagent in an agglutination test, the method including the steps of:
   combining the sample with the rapid plasma antigen reagent, the rapid plasma antigen reagent including contrasting visibility particles therein;
   locating the sample and reagent in liquid form on a substrate, the combined sample and reagent having a circular shape on the substrate;
   rotating the substrate to cause the contrasting visibility particles to form at least a portion of a ring within the circular shape; and
   evaluating the ring to determine if the sample is reactive or non-reactive, wherein a ring comprising dispersed clumps of particles is indicative of a reactive sample and a substantially uniform ring without clumping is indicative of a non-reactive sample.

2. The method of claim 1 wherein said locating steps includes the sample and the rapid plasma antigen reagent in a common contained space.

3. The method of claim 2 wherein said common contained space being one of a plurality of wells in a microtiter plate.

4. The method of claim 3 wherein the wells have a concave bottom.

5. The method of claim 2 wherein said locating step includes sequentially placing the sample and the rapid plasma antigen reagent into the contained space.

6. The method of claim 1 wherein said rotating step includes rotating by an eccentric mass on a rotating output shaft of a motor, and with the motor coupled at least indirectly to the substrate comprising a contained space where the sample and the rapid plasma antigen reagent are located.

7. The method of claim 6 wherein the radius of the eccentric mass away from the output shaft of the motor is between about 5 millimeters and 15 millimeters horizontally, so that the amplitude of the rotating is between about 5 millimeters and 15 millimeters and wherein the contained space has a size of up to about 15 millimeters in diameter.

8. The method of claim 7 wherein said rotating step includes the eccentric mass located about 10 millimeters horizontally away from the output shaft of the motor and rotating occurs at about 100 revolutions per minute.

9. The method of claim 1 wherein said evaluating step includes visual evaluation of the sample after said rotating step by a human eye.

10. The method of claim 1 wherein said evaluating step includes automated evaluation by photographing the sample and rapid plasma antigen reagent after said combining step and said rotating step; processing an image produced by said photographing step to determine if the sample is reactive or non-reactive.

11. The method of claim 10 wherein processing said image includes production of a digital image, the digital image processed by having a curve fitted to the ring within the digital image, multiple radial lines substantially perpendicular to the curve evaluated for darkness of pixels within the digital image which fall along the radial lines, quantifying variation of darkness of pixels along the radial lines, averaging of darkness variations of said quantifying step with darkness variation values of adjacent radial lines, calculating a difference between darkness variation of said quantifying step for each radial line and an average of darkness variation values of adjacent radial lines, and correlating this difference of said calculating step with clumpiness of the sample.

12. The method of claim 11 wherein the differences of said calculating step are each correlated into separate bins of data having similar values, with radial lines having lowest difference grouped together and radial lines having highest difference grouped together, and radial lines having similar intermediate differences grouped together, and counting the number of lines associated with each of the bins.

13. The method of claim 11 wherein said multiple radial lines substantially perpendicular to said curve include at least 360 radial lines which are each at least 20 pixels long.

14. The method of claim 11 wherein regions of the digital image outside of the multiple radial lines substantially perpendicular to the curve are evaluated similarly to the radial lines which intersect the curve, to identify regions of dumpiness outside of the curve fitted to the ring within the digital image.

15. The method of claim 11 including the further step of comparing known reactive and non-reactive sample data sets processed through said evaluating step with a new digital image processed through said evaluating step to correlate the new digital image to those known to be reactive or non-reactive and to similarly score the new digital image as representative of a correspondingly reactive or non-reactive result.

16. The method of claim 15 wherein said comparing step includes processing the known data set by production of a digital image, the digital image processed by having a curve fitted to the ring of dark high visibility particles within the digital image, multiple radial lines substantially perpendicular to the curve evaluated for darkness of pixels within the digital image which fall along the radial lines, quantifying variation of darkness of pixels along the radial lines, averaging of darkness variations of said quantifying step with darkness variation values of adjacent radial lines, calculating a difference between darkness variation of said quantifying step for each radial line and an average of darkness variation values of adjacent radial lines, and correlating this difference of said calculating step with dumpiness of the sample, and further grouping the differences between radial line darkness variation and an average of darkness variation of adjacent lines into separate bins of data having similar values, including evaluation of regions of the digital image outside of the curve fit to the digital image data, and with the radial lines substantially perpendicular to the curve including at least 360 radial lines and similarly processing the new image with similar results in evaluating the new image scored similarly to produce a similar conclusion with those of the known data set.

17. The method of claim 16 including the further step of evaluating the standard deviation of the darkness variation values quantified relative to darkness variation values of other adjacent radial lines.

18. The method of claim 17 including the further step of evaluating area under a curve plotting the darkness variation values quantified relative to other adjacent radial lines.

19. The method of claim 18 including the further step of providing a plurality of separate bins into which similar data is correlated for each of the radial lines.

20. The method of claim 19 including the further step of providing at least six separate ones of the bins and evaluating the sum of the last three of the at least six bins representative of the highest difference in darkness variation of each radial line relative to an average of adjacent radial lines.

\* \* \* \* \*